US009096536B2

United States Patent
Borowski et al.

(10) Patent No.: US 9,096,536 B2
(45) Date of Patent: Aug. 4, 2015

(54) ASYMMETRICALLY SUBSTITUTED ANTHRAPYRIDAZONE DERIVATIVES AS CYTOSTATICS

(75) Inventors: Edward Borowski, Gdansk (PL); Barbara Stefanska, Warsaw (PL); Maria Dzieduszycka, Sopot (PL); Marcin Cybulski, Warsaw (PL); Wieslaw Szelejewski, Warsaw (PL); Janusz Obukowicz, Stare Babice (PL); Maria Bontemps-Gracz, Gdansk (PL); Malgorzata Wysocka, Gdansk (PL); Jan Mazerski, Gdansk (PL); Pawel Punda, Szczytno (PL); Joanna Wietrzyk, Wroclaw (PL)

(73) Assignee: BS-154 S.P. ZO.O., Gdansk (PL)

( * ) Notice: Subject to any disclaimer, the term of this patent is extended or adjusted under 35 U.S.C. 154(b) by 0 days.

(21) Appl. No.: 14/111,022

(22) PCT Filed: Apr. 13, 2012

(86) PCT No.: PCT/PL2012/000025
§ 371 (c)(1),
(2), (4) Date: Oct. 10, 2013

(87) PCT Pub. No.: WO2012/141604
PCT Pub. Date: Oct. 18, 2012

(65) Prior Publication Data
US 2014/0031357 A1    Jan. 30, 2014

(30) Foreign Application Priority Data

Apr. 14, 2011 (PL) .......................... 394569

(51) Int. Cl.
*C07D 237/26* (2006.01)
*C07D 487/06* (2006.01)
*A61K 31/502* (2006.01)
*A61K 31/5025* (2006.01)
*C07D 237/36* (2006.01)

(52) U.S. Cl.
CPC ............ *C07D 237/26* (2013.01); *A61K 31/502* (2013.01); *A61K 31/5025* (2013.01); *C07D 237/36* (2013.01); *C07D 487/06* (2013.01)

(58) Field of Classification Search
USPC .......................................... 514/248; 544/233
See application file for complete search history.

(56) References Cited

PUBLICATIONS

Stefanska et al., Synthesis and Biological Evaluation of 2,7-Dihydro-3H-dibenzo[de,h]cinnoline-3,7-dione Derivatives, a Novel Group of Anticancer Agents Active on a Multidrug Resistant Cell Line, 2003, Bioorganic & Medicinal Chemistry, 11, 561-572.*
International Search Report for PCT/PL2012/000025 mailed Sep. 27, 2012.
Dzieduszycka, et al.; "Synthesis of New Polycyclic Anthracenedione Analogs with Hetero- or Carbocyclic Ring(s) Fused to the Chromophore System"; Polish Journal of Chemistry, 2007; pp. 535-545; vol. 81.
Borowski, et al.; "Strategies for overcoming ABC-transporters-mediated multidrug resistance (MDR) of tumor cells"; Acta Biochimica Polonica, 2005; pp. 609-627; vol. 52, Nr: 3.
Dokunikhin, et al.; "Pyridazoneanthrone and its derivatives I"; Zhurnal Obshchei Khimii; 1964; pp. 2372-2374; vol. 34; No. 7.
Krapcho et al; "6,9-Bis[(aminoalkyl)amino]benzo[g]isoquinoline-5,10-diones. A Novel Class of Chromophore-Modified Antitumor Anthracene-9,10-diones: Synthesis and Antitumor Evaluations", J. Med. Chem., 1994; pp. 828-837; vol. 37.
Seelig, A; "A general pattern for substrate recognition by P-glycoprotein"; Eur. J. Biochem, 1998; pp. 252-261; vol. 251.
Stefanska, et al; "6-[(Aminoalkyl)amino]-Substituted 7H-Benzo[e]perimidin-7-ones as Novel Antineoplastic Agents. Synthesis and Biological Evaluation"; J. Med. Chem., 1993; pp. 38-41; vol. 36.
Gandolfi, et al. Chromophore-Modified Antitumor Anthracenediones: Synthesis, DNA Binding, and Cytotoxic Activity of 1,4-Bis[(aminoalkyl)amino]benzo[g]phthalazine-5,10-diones; J. Med. Chem., 1995; pp. 526-536; vol. 38.
Showalter, et al; "Design, biochemical pharmacology, electrochemistry and tumour biology of anti-tumour anthrapyrazoles"; Anti-Cancer Drug Design, 1986; pp. 73-85; vol. 1.
Stefanska, et al.; "Synthesis and Biological Evaluation of 2,7-Dihydro-3H-dibenzo[de,h]cinnoline-3,7-dione Derivatives, a Novel Group of Anticancer Agents Active on a Multidrug Resistant Cell Line" Bioorganic & Medicinal Chemistry, 2003; pp. 561-572; vol. 11.

* cited by examiner

*Primary Examiner* — Kristin Vajda
(74) *Attorney, Agent, or Firm* — Walker & Jocke

(57) ABSTRACT

The invention relates to the new, asymmetrically substituted derivatives of 2,7-dihydro-3H-dibenzo[de,h]cinnoline-3,7-dione and their use as cytostatics exhibiting activity against tumor cells, especially against cells with multidrug resistance (MDR). In particular, the invention concerns derivatives of 2,7-dihydro-3H-dibenzo[de,h]cinnoline-3,7-dione represented by the general formula (I).

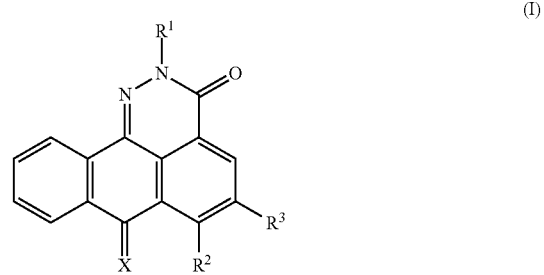

15 Claims, 4 Drawing Sheets

ASYMMETRICALLY SUBSTITUTED ANTHRAPYRIDAZONE DERIVATIVES AS CYTOSTATICS

FIELD OF THE INVENTION

The invention relates to the new, asymmetrically substituted derivatives of 2,7-dihydro-3H-dibenzo[de,h]cinnoline-3,7-dione and their use as cytostatics exhibiting activity against tumor cells, especially against cells with multidrug resistance (MDR). In particular, the invention concerns derivatives of 2,7-dihydro-3H-dibenzo[de,h]cinnoline-3,7-dione represented by the general formula (I), named further as anthrapyridazone derivatives.

BACKGROUND OF THE INVENTION

Synthetic derivatives and analogs of anthraquinone are a valuable group of cytostatics. Among developed compounds of this type, 1,4-dihydroxy-5,8-bis[2-(2-hydroxyethylamino) ethylamino]-9,10-anthracenodione, known under the International Non-proprietary Name (INN) mitoxantrone, is in clinical use as antitumor drug. However, appearance of phenotypic, multidrug cross resistance of tumor cells (MultiDrug Resistance—MDR), causes the loss of therapeutic efficacy of antitumor drugs, even chemically and functionally unrelated ones, including mitoxantrone.

The phenomenon of MDR depends on overexpression of genes coding for membrane proteins exporting from cell xenobiotics such as cytostatics and thus preventing from retaining therapeutic concentration of drug in cell. Three groups of such glycoprotein type proteins have been discovered, among them MDR-1 (so called P-gp), BCRP protein and MRP proteins group. These proteins differ by their substrate spectrum towards cytostatics interacting with them. However, this spectrum is very broad and includes many structural groups of antitumor chemotherapeutics.

The phenomenon of multidrug resistance prompts the necessity of searching for new cytostatics which would be active against the resistant cells, including also anthraquinone group drugs. Different strategies for the design of these compounds were developed (E. Borowski et al., Acta Biochim. Polon. 52, 609, 2005). The most promising strategy concerns the design of compounds which are poor substrates of proteins responsible for MDR phenomenon. This strategy gives the best chance to improve drug selectivity and reduce the adverse side effects. Considering however very broad substrate spectrum of MDR proteins the effects of these studies are not satisfactory up to now. It was found that antymetabolites as 5-fluorouracil, are not recognizable by xenobiotics exporting MDR pomps because of their structural similarity to natural metabolites uracil. Only a few other antitumor drugs have been shown to be rather poor substrates for MDR pomps. One important exception is taxol, which however is the MDR-1 pomp substrate, but is not the substrate of MRP pomp and thus exhibits activity towards tumor cells with overexpression of this pomp.

Among important group of cytostatics the analogs and derivatives of antraquinone, none of them has been as yet introduced to clinical practice, for the treatment of drug resistant tumors.

Until now, among synthesized mitoxantrone analogs and derivatives, some activity in relation to resistant cells show compounds, possessing an additional heterocycling ring fused to the anthraquinone moiety. They are compounds with pyrazole ring fused to the chromophore system (H. Showalter et al., Anti-Cancer Drug Design 1, 73, 1986), pyridine ring (P. Krapcho et al., J. Med. Chem., 37, 823, 1994), pyridazone ring (C. Gandolfii, J. Med. Chem. 38, 526, 1995), pyrimidine ring (B. Stefańska et al., J. Med. Chem. 36, 38, 1993) or pyridazone ring i. e. anthrapyridazone derivatives (B. Stefańska et al., Bioorg. Med. Chem., 11, 561, 2003).

Among antrapyridazones described in Bioorg. Med. Chem., 11, 561, 2003, revealed are derivatives symmetrically di- substituted at positions 2- and 6- with dimethylaminoethyl or piperidineethyl moieties. Also one asymmetrically substituted compound with dimethylaminoethyl group at position 2- and piperidineethyl group at position 6- has been described. Some of these derivatives exhibited some in vitro cytotoxic activity against selected tumor cells, such as murine leukemia L1210 cells and human K562, but low activity against multidrug resistant subline of human leukemia K562/DX. There are no data on the activity of these compounds towards the cells of solid tumors.

In Dzieduszycka's et al. publication, Polish J. Chem., 81, 535, 2007, the synthesis of pentacyclic anthrapyridazone analogs with additional ring forming imidazole or phthalazine system has been described, however, no data on the biological properties of obtaining compounds are shown.

The new compounds according to the present invention, being assymmetrically substituted anthrapyridazone derivatives, exhibit significant cytotoxic activity towards multidrug resistant tumor cells. For the first time it was found that among anthrapyridazone analogs and derivatives this activity results from the fact that they are poor MDR exporting proteins substrates. As mentioned above this is the advantageous mechanism of counteraction to the activity of pomp exporting cytostatic from cells. This way of activity of anthrapyridazone derivatives, especially asymmetrically substituted ones till now has not been known.

THE SUMMARY OF THE INVENTION

The present invention provides asymmetrically substituted anthrapyridazone derivatives represented by formula (I)

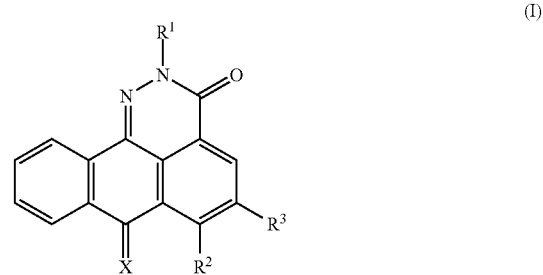

(I)

wherein
X is oxygen or nitrogen atom,
and
when X is oxygen atom, then anthrapyridazone is presented by formula (IA)

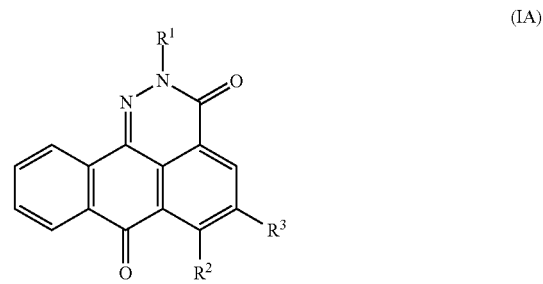

(IA)

wherein one of three substituents $R^1$, $R^2$ or $R^3$ is hydrogen atom, while two remaining once, if are not hydrogen atoms, have the following meaning:

$R^1$ is $(CH_2)_q$—OH or —$(CH_2)_q$—$N(R^4)$—$R^5$,
where
q=2 or 3;
$R^4$ and $R^5$ are the same and mean $C_1$-$C_3$-alkyl,
or
$R^4$ and $R^5$ together with the nitrogen atom at position 2 to which they are attached form 6-membered cyclic ring optionally containing additional nitrogen or oxygen atoms, such as piperazine, piperidine or morpholine rings;

$R^2$ is —NH—$(CH_2)_m$—$(Y)_n$—$(CH_2)_p$—$R^6$,
where
m=0,1,2 or 3
n=0 or 1
p=0,1 or 2
Y is —C(O)— or —$N(R^7)$—
$R^6$ is H, —OH or phenyl,
$R^7$ is hydrogen atom or $C_1$-$C_3$-alkyl, $R^3$ is hydrogen atom or —NH—$(CH_2)_r$—$N(R^8)$—$R^9$ moiety
where
r=1,2 or 3,
$R^8$ and $R^9$ are the same or different and independently are H, $C_1$-$C_3$-alkyl or phenyl substituted with $C_1$-$C_3$-alkyl;
with the provision, that
when $R^1$ is —$(CH_2)_2N(CH_3)_2$ (q=2 and $R^4$=$R^5$=$CH_3$), then $R^2$ is not —$(CH_2)_2N(CH_3)_2$ nor —$NH_2$ (m≠0, n≠1, $R^6$≠H and $R^7$≠H);
and
when X is nitrogen atom, then in formula (I)
$R^3$ is H,
$R^2$ is attached to nitrogen atom and together form the group presented by formula (a) or (b)

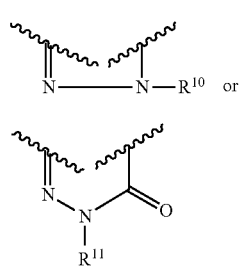

$R^1$ and $R^{10}$ are the same and are —$(CH_2)_2N(CH_3)_2$, and $R^1$ and $R^{11}$ are the same and are —$(CH_2)_2N(CH_2CH_3)_2$, thus anthrapyridazone has the formula (I B) or (I C)

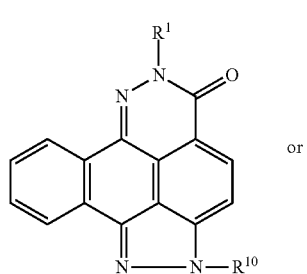

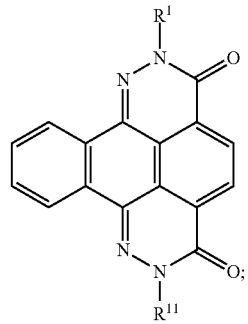

as well as their pharmaceutically acceptable salts.

Anthrapyridazone derivatives of formula (I) exhibit significant cytostatic activity in regards to multidrug resistant (MDR) tumor cells involving standard cell lines with overexpression of different exporting pumps, MDR-1, BCRP and MRP, as well as, broad spectrum resistant cell lines derived from different tissues and organs of patients.

Anthrapyridazone derivatives according to the invention are potential medicines exhibiting activity towards MDR resistant tumor cells.

Due to that, the invention provides further anthrapyridazone derivatives of formula (I) for use as medicines exhibiting the activity against tumor cells, especially multidrug resistant ones.

In particular, the invention provides anthrapyridazone derivatives of formula (I) for use as the medicines for the treatment of neoplastic diseases in such oncologic patients for whose the resistance towards earlier used chemotherapeutics, especially anthraquinone ones, like anthracycline and mitoxantrone, has been established.

The invention provides further anthrapyridazone derivatives of formula (I) as the medicines for use together with other chemotherapeutics in the treatment of patients with neoplastic diseases with resistance to earlier used chemotherapeutics, including resistance due to overexpression of exporting proteins, as P-gp, BCRP and MRP. Anthrapyridazone derivatives are particularly active against tumor cell with overexpression of P-gp and BCRP protein, but less active against tumor cells with overexpression of MRP protein. In this case it seems to be advantageous the combined therapy with anthrapyridazone derivatives and taxoides, which are active towards tumor cells due to overexpression of MRP protein. Combination of anthrapyridazone and taxoides in one pharmaceutical formulation allows to exhibit cytostatic activity against tumor cells including broad spectrum of resistance, together with the resistance due to the overexpression MRP protein.

Although it is possible to administer anthrapyridazone derivatives (I) to patients per se, generally they could be used in form of pharmaceutical formulations, by adequate for the given clinical case route.

Thus, the other aspect of the invention is the pharmaceutical formulation comprising as active substance anthrapyridazone of formula (I) in therapeutically effective amount together with pharmaceutically acceptable carriers and/or auxiliary substances.

One more aspect of the invention is the method of patients treatment, comprising administering to the individual in the need of such treatment of therapeutically effective amount of anthrapiridazone of formula (I).

THE DETAILED DESCRIPTION OF THE INVENTION

Figure 1:
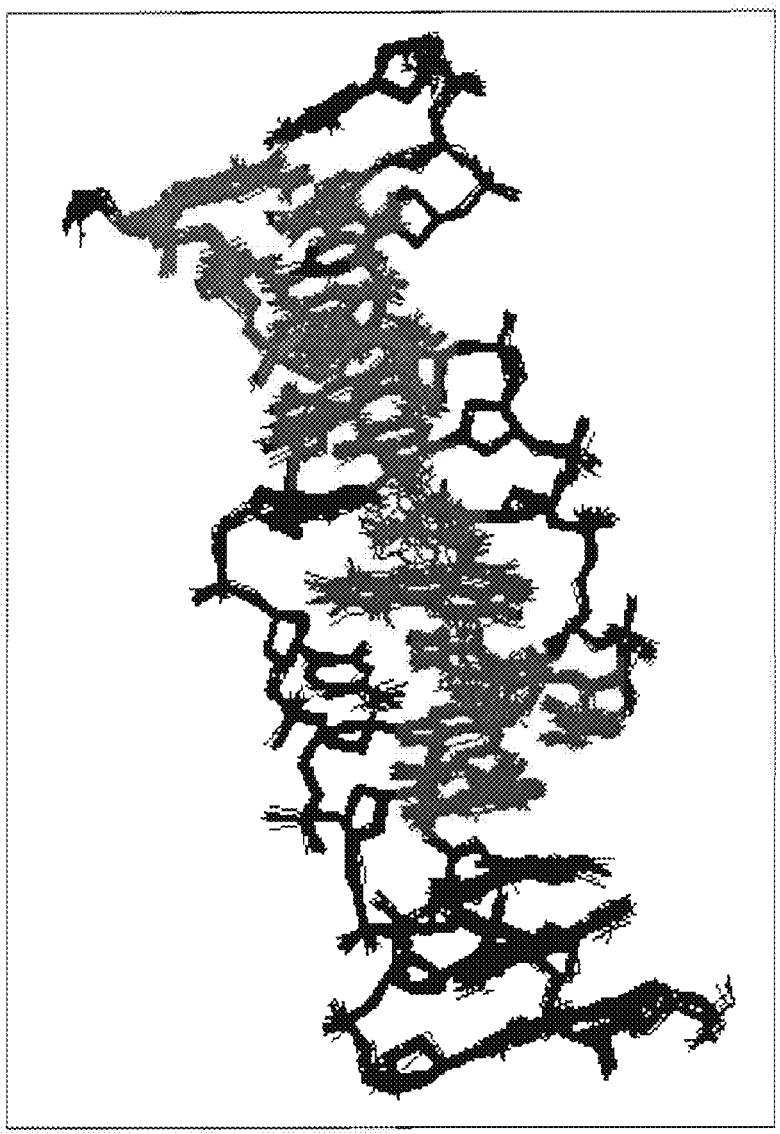
FIG. 1 illustrates the molecular structure of exemplary intercalating complex of compound BS-121 with DNA, calculated by molecular modeling methods.

In one aspect of the invention 2,6disubstituted anthrapyridazone derivatives have the formula (IA),

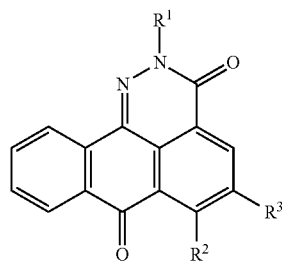

(IA)

wherein
$R^1$ is —$(CH_2)_2N(CH_3)_2$,
$R^2$ is —NH—$(CH_2)_m$—$(Y)_n$—$(CH_2)_p$—$R^6$,
where
  m=0, 1, 2 or 3
  n=0, 1
  p=0, 1, 2
  Y is —$N(R^7)$—
  $R^6$ is hydrogen atom or —OH, and
  $R^7$ is hydrogen atom or $C_1$-$C_3$-alkyl, and
$R^3$ is hydrogen atom.

In another preferred embodiment of the invention 2,6-disubstituted anthrapyridazone derivatives have the formula (IA), wherein
$R^1$ is —$(CH_2)_q$—$N(R^4)$—$R^5$,
where
  q=2 or 3,
  $R^4$ and $R^5$ together with nitrogen atom at position 2, to which they are attached, form 6-membered cyclic ring eventually containing additional nitrogen or oxygen atom, such as piperazine, piperidine or morpholine rings;
$R^2$ is —NH—$(CH_2)_m$—$(Y)_n$—$(CH_2)_p$—$R^6$,
where
  m=0, 1, 2 or 3,
  n=0, 1,
  p=0, 1, 2,
  Y is —$N(R^7)$—,
  $R^6$ is hydrogen atom or —OH,
  $R^7$ is hydrogen atom or —$CH_3$, and
$R^3$ is hydrogen atom.

In another preferred embodiment of the invention 5-monosubstituted anthrapyridazone derivatives have the formula (IA), wherein
$R^1$ is hydrogen atom,
$R^2$ is —NH—$(CH_2)_m$—$(Y)_n$—$(CH_2)_p$—$R^6$,
where
  m=0, 1, 2 or 3,
  n=0 or 1,
  p=0, 1 or 2,
  Y is —$N(R^7)$—,
$R^6$ is hydrogen atom or —OH,
$R^7$ is hydrogen atom or —$CH_3$, and
$R^3$ is hydrogen atom.

In further preferred embodiment of the invention, 2,5-disubstituted anthrapyridazone derivatives have the formula (IA), wherein
$R^1$ is —$(CH_2)_2N(CH_3)_2$,
$R^2$ is hydrogen atom, and
$R^3$ is hydrogen atom or —NH—$(CH_2)_r$—$N(R^8)$—$R^9$,
where
  r=2,
  $R^8$ and $R^9$ are the same or different and independently are hydrogen atom, $C_1$-$C_3$-alkyl or $C_1$-$C_3$-phenyl.

The following advantageous compounds according to the invention are pentacyclic anthrapyridazone derivatives containing imidazole or phtalazine ring, presented by formulas (IB) and (IC);

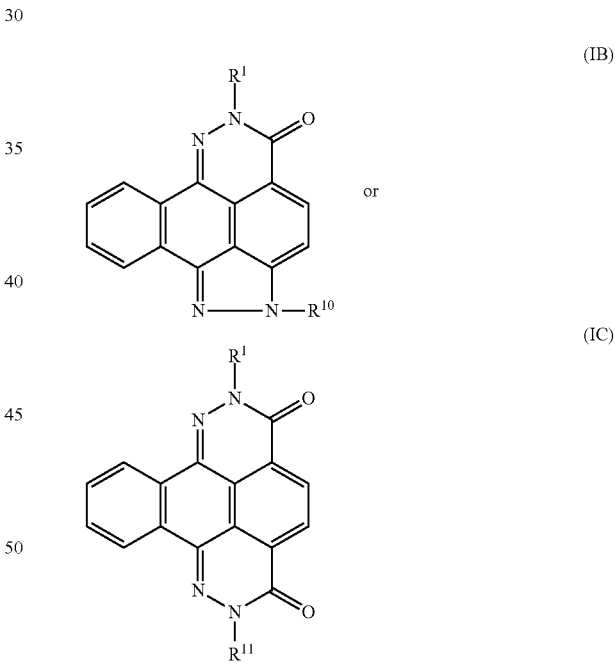

where
$R^1$ and $R^{10}$ are the same and represent —$(CH_2)_2N(CH_3)_2$, and
$R^1$ and $R^{11}$ are the same and represent —$(CH_2)_2N(CH_2 CH_3)_2$.

Especially active anthrapyridazone derivatives are compounds of formula (I), chosen from a group comprising:
2-[2-(Dimethylamino)ethyl]-6-{[2-(methylamino)ethyl]amino}-2,7-dihydro-3H-dibenzo[de,h]cynnoline-3,7-dione (BS-154),
2-[2-(Dimethylamino)ethyl]-6-[2-(aminoethyl)amino)-2,7-dihydro-3H-dibenzo[de,h]cynnoline-3,7-dione (BS-121), 2-[2-(Dimethylamino)ethyl]-6-(N-methylamino)-2,7-dihydro-3H-dibenzo[de,h]cynnoline-3,7-dione (PDZ-7), 2-[2-(Dimethylamino)ethyl]-6-{[2-(ethylamino)ethyl]amino}-2,7-dihydro-3H-dibenzo[de,h]cynnoline-3,7-dione (C-180), 2-[2-(Dimethylamino)ethyl]-6-[(3-aminopropyl)amino]-2,7-dihydro-3H-dibenzo[de,h]cynnoline-3,7-dione (PDZ-20), 2-[2-(Dimethylamino)ethyl]-6-[(3-acetylaminopropyl)amino]-2,7-dihydro-3H-dibenzo[de,h]cynnoline-3,7-dione (PDZ-13), 2-[2-(Dimethylamino)ethyl]-6-(acetylamino)-2,7-dihydro-3H-dibenzo[de,h]cynnoline-3,7-dione (PDZ-14), 2-[2-(Dimethylamino)ethyl]-6-{[(2-diethylamino)ethyl]amino}-2,7-dihydro-3H-dibenzo[de,h]cynnoline-3,7-dione (C-155), 2-[2-(Dimethylamino)ethyl]-6-(N-benzylamino)-2,7-dihydro-3H-dibenzo[de,h]cynnoline-3,7-dione (PDZ-8), 2-[2-(Dimethylamino)ethyl]-6-[2-(2-aminoethylamino)ethanolo]-2,7-dihydro-3H-dibenzo[de,h]cynnoline-3,7-dione (C-165), 2-[2-(Dimethylamino)ethyl]-6-[(N,N-dimethylacetamido)amino]-2,7-dihydro-3H-dibenzo[de,h]cynnoline-3,7-dione (PDZ-12), 2-[2-(Dimethylamino)propyl]-6-{[2-(dimethylamino)propyl]amino}-2,7-dihydro-3H-dibenzo[de,h]cynnoline-3,7-dione (C-123), 2-(2-Morpholinoethyl)-6-amino-2,7-dihydro-3H-dibenzo[de,h]cynnoline-3,7-dione (PDZ-4), 2-[3-(Dimethylamino)propyl]-6-amino-2,7-dihydro-3H-dibenzo[de,h]cynnoline-3,7-dione (PDZ-3), 2-[2-(Piperidinamino)ethyl]-6-amino-2,7-dihydro-3H-dibenzo[de,h]-cynnoline-3,7-dione (PDZ-5), 2-(2-Hydroksyethyl)-6-(2-dimethylamino)ethylamino-2H-dibenzo[de,h]cynnoline-3,7-dione (C-167), 2-[2-(Piperidinamino)ethyl]-6-(2-benzylaminoethylamino)-2,7-dihydro-3H-dibenzo[de,h]cynnoline-3,7-dione (PDZ-17), 6-(2-Diethylaminoethylamino)-2,7-dihydro-3H-dibenzo[de,h]cynnoline-3,7-dione (PDZ-18), 6-(2Benzylaminoethylamino)-2,7-dihydro-3H-dibenzo[de,h]cynnoline-3,7-dione (PDZ-10), 6-2Butylaminoethylamino)-2,7-dihydro-3H-dibenzo[de,h]cynnoline-3,7-dione (PDZ-9), 6-[(3Dimethylamino)propyl]amino-3H-dibenzo[de,h]cynnoline-3,7-dione (C-131), 2[2(Dimethylamino)ethyl]-2,7-dihydro-3H-dibenzo[de,h]cynnoline-3,7-dione (PDZ-15), 2-[2-(Dimethylamino)ethyl]-5-[2-(diethylamino)ethyl]-2,7-dihydro-3H-dibenzo [de,h]ynnoline-3,7-dione (C-169), 2-[2-(Dimethylamino)ethyl]-5-(2-aminoethylamino)-2,7-dihydro-3H-dibenzo [de,h]cynnoline-3,7-dione (C-170),

[2-(Dimethylamino)ethyl]-5-[(2-benzyloamino)ethylamino]-2-2,7-dihydro-3H-dibenzo[de,h]cynnoline-3,7dione (C-171), Bis-2,6-[2(Dimethylamino)ethyl]-2,6-dihydro-5H-benzo[h]indazolo[5,4,3-def]cynnolin-5-one (C-163), and 2,7-Bis-[2-(Diethyloamino)ethyl]-2,7-dihydrobenzo[h]ftalazyno[7,8,1-def]cynnoline-3,6-dione (CP-4).

The most preferred anthrapyridazone derivatives of formula (I) in respect of pharmacological properties are:

2-[2-(dimethylamino)ethyl]-6-{[2-(methylamino)ethyl]amino}-2,7-dihydro-3-H-dibenzo[de,h]cynnoline-3,7-dione (BS-154) and 2-[2-(dimethylamino)ethyl]-6-[2-(aminoethyl)]-2,7-dihydro-3H-dibenzo[de,h]cynnoline-3,7-dione (BS-121).

Structures of the obtained active anthrapyridazone derivatives of the invention are summarized in the tables below:

TABLE 1

Anthrapyridazone derivatives of formula (IA):

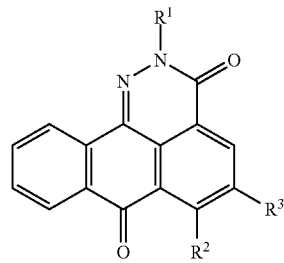

(IA)

| Ex. | Symbol | $R^1$ | R2 | $R^3$ |
|---|---|---|---|---|
| 2 | BS-154 | $(CH_2)_2N(CH_3)_2$ | $NH(CH_2)_2NHCH_3$ | H |
| 3 | BS-121 | $(CH_2)_2N(CH_3)_2$ | $NH(CH_2)_2NH_2$ | H |
| 4 | PDZ-7 | $(CH_2)_2N(CH_3)_2$ | $NHCH_3$ | H |
| 5 | C-180 | $(CH_2)_2N(CH_3)_2$ | $NH(CH_2)_2NHC_2H_5$ | H |
| 6 | PDZ-20 | $(CH_2)_2N(CH_3)_2$ | $NH(CH_2)_3NH_2$ | H |
| 7 | PDZ-13 | $(CH_2)_2N(CH_3)_2$ | $NH(CH_2)_3NHC(O)CH_3$ | H |
| 8 | PDZ-14 | $(CH_2)_2N(CH_3)_2$ | $NHC(O)CH_3$ | H |
| 9 | C-155 | $(CH_2)_2N(CH_3)_2$ | $NH(CH_2)_2N(C_2H_5)_2$ | H |
| 10 | PDZ-8 | $(CH_2)_2N(CH_3)_2$ | $NHCH_2C_6H_5$ | H |
| 11 | C-165 | $(CH_2)_2N(CH_3)_2$ | $NH(CH_2)_2NH(CH_2)_2OH$ | H |
| 12 | PDZ-12 | $(CH_2)_2N(CH_3)_2$ | $NHCH_2C(O)N(CH_3)_2$ | H |
| 13 | C-123 | $(CH_2)_3N(CH_3)_2$ | $NH(CH_2)_3N(CH_3)_2$ | H |
| 14 | PDZ-4 | $(CH_2)_2$-c-$N(CH_2)_4O$ | $NH_2$ | H |
| 15 | PDZ-3 | $(CH_2)_3N(CH_3)_2$ | $NH_2$ | H |
| 16 | PDZ-5 | $(CH_2)_2$-c-$N(CH_2)_5$ | $NH_2$ | H |
| 17 | C-167 | $(CH_2)_2OH$ | $NH(CH_2)_2N(CH_3)_2$ | H |
| 18 | PDZ-17 | $(CH_2)_2$-c-$N(CH_2)_5$ | $NH(CH_2)_2NHCH_2C_6H_5$ | H |

TABLE 1-continued

Anthrapyridazone derivatives of formula (IA):

(IA)

| Ex. | Symbol | R¹ | R2 | R³ |
|---|---|---|---|---|
| 19 | PDZ-18 | H | $NH(CH_2)_2N(C_2H_5)_2$ | H |
| 20 | PDZ-10 | H | $NH(CH_2)_2NHCH_2C_6H_5$ | H |
| 21 | PDZ-9 | H | $NH(CH_2)_2NH(CH_2)_3CH_3$ | H |
| 22 | C-131 | H | $NH(CH_2)_3N(CH_3)_2$ | H |
| 23 | PDZ-15 | $(CH_2)_2N(CH_3)_2$ | H | H |
| 25 | C-169 | $(CH_2)_2N(CH_3)_2$ | H | $NH(CH_2)_2N(C_2H_5)_2$ |
| 26 | C-170 | $(CH_2)_2N(CH_3)_2$ | H | $NH(CH_2)_2NH_2$ |
| 27 | C-171 | $(CH_2)_2N(CH_3)_2$ | H | $NH(CH_2)_2NHCH_2C_6H_5$ |

TABLE 2

Anthrapyridazone derivatives comprising fused heterocyclic ring:

(IB)

(IC)

| Ex. | Symbol | R¹ | R¹⁰ | R¹¹ |
|---|---|---|---|---|
| 28 | C-163 | $-(CH_2)_2N(CH_3)_2$ | $-(CH_2)_2N(CH_3)_2$ | — |
| 29 | CP-4 | $-(CH_2)_2N(C_2H_5)_2$ | — | $-(CH_2)_2N(C_2H_5)_2$ |

Anthrapyridazone derivatives of formula (I) according to the invention can be synthesized following the methods generally described in the literature.

Tetracyclic anthrapyridazone derivatives substituted at positions 2- and 6-, presented by formula (I), where X is O, and the meaning of substituent R¹ and R² is the same as in formula (IA), could be synthesized in the manner described in Bioorg. Med. Chem., 11, 561, 2003, according to Scheme 1.

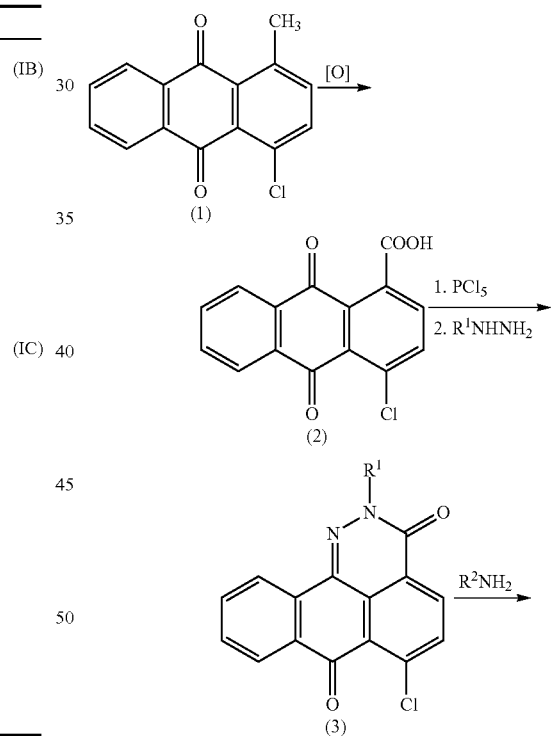

SCHEME 1

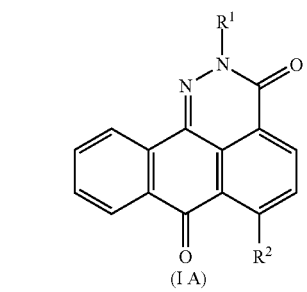

4-Chloroanthraquinone-1-carboxylic acid (2) obtained by oxidation of 1-chloro-4-methylarithraquinone, is converted into respective acid chloride and cyclized with alkyl hydrazine to anthrapyridazone derivatives (3) substituted at position 2-with alkylamino group. Next, derivative (3) in the reaction with amine in pyridine or neutral solvent is substituted at position 6-.

In the similar manner tetracyclic anthrapyridazone derivatives disubstituted at positions 2- and 5-, presented by formula (I), were synthesized, where X is O, and the meaning of $R^1$ and $R^3$ are the same as described for formula (IA), as is illustrated on Scheme 2 below.

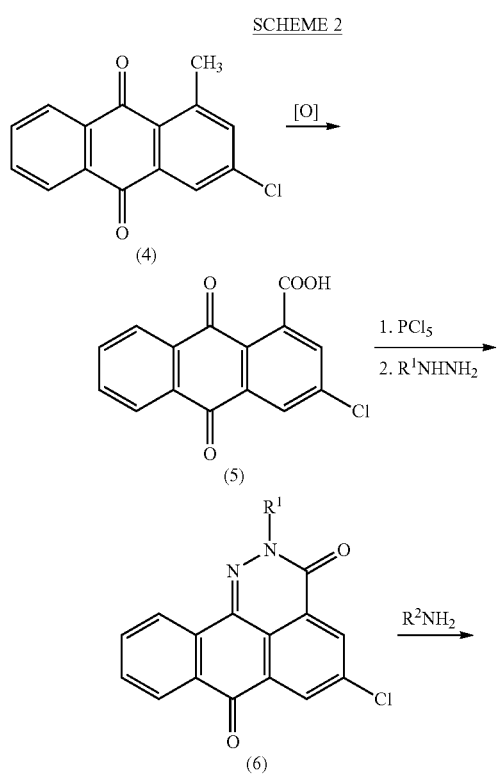

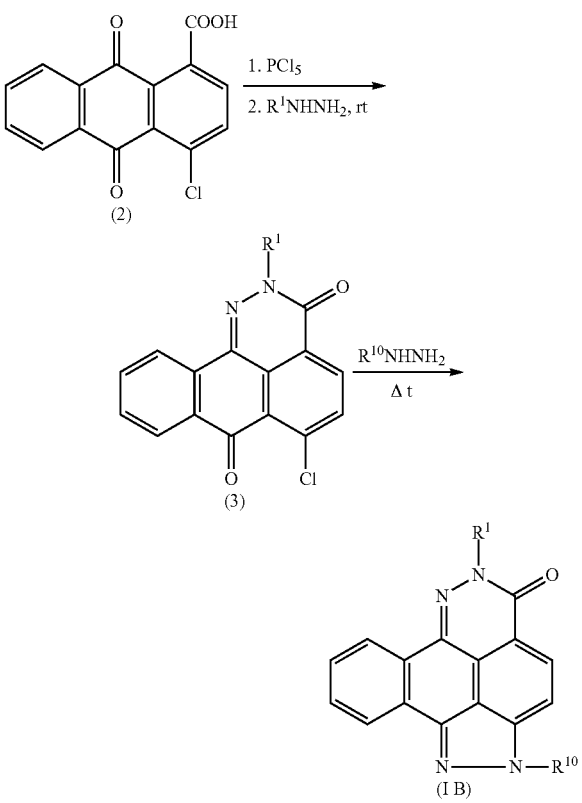

Phthalazine-anthraquinone derivatives of formula (IC), wherein $R^1$ and $R^{11}$ are the same, could be obtained following the method described in Polish J. Chem. 81, 535, 2007, as shown on Scheme 4 below. The substrate 9,10-dioxo-9,10-dihydro-1-anthraceno-1,4-dicarboxylic acid (5) is converted into its acid chloride and cyclized with molar excess of dialkylaminoethylhydrazine.

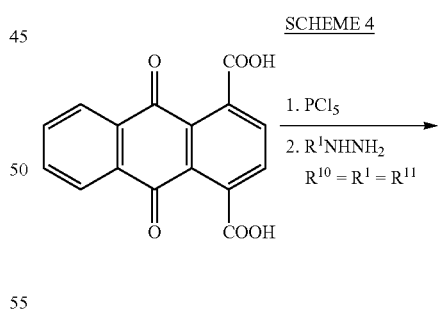

Pentacyclic-indazolo derivative of anthraquinone of formula (IB), where $R^1$ and $R^{10}$ are the same, according to Scheme 3 below, is synthesized from 4-chloroanthraquinone-1-carboxylic acid (2). The cyclization with alkyloamino-hydrazine derivative at room temperature results in anthrapyridazone derivative substituted at position 2 by alkylamino group. Next, in the reaction of (3) with dialkylaminoethylhydrazine, in high boiling point aprotonic solvent at elevated temperature, pyrazole ring condensed with chromophore is obtained.

Anthrapyridazone derivatives of formula (I) can exist as tautomers or optical isomers. All isomers and tautomers of those compounds are included within the range of this invention. Individual optical isomers or enantiomers can be obtained by the methods well known in the art, like chiral HPLC, enzymatic cleavage or may be obtained by using the methods of stereoselective synthesis.

Anthrapyridazone derivatives of formula (I) easily form the pharmaceutically acceptable salts with acids. "Pharmaceutically acceptable salt" means the salt derived from pharmaceutically acceptable mineral or organic acid. Examples of suitable acids include hydrochloride, hydrobromic, sulphuric, nitric, perchloric, fumaric, maleic, phosphoric, glycolic, lactic, adipic, ascorbic, salicylic, ethylenedicarboxylic, tartaric, acetic, citric, formic, benzoic, malonic, p-toluenesulphonic, methanesulphonic, naphthalene-2-sulphonic, benzenesulphonic acids and the others. Others acids, such as oxalic acid, although are not pharmaceutically acceptable, can be useful in the process of preparation compounds according to the invention and their purification.

Especially preferred salts of anthrapyridazone derivatives of formula (I) are hydrochlorides.

Anthrapyridazone derivatives of formula (I) can be used in therapy alone or in the combination with other chemotherapeutics, in therapeutically effective amounts, in the treatment of patients with neoplastic diseases when the resistance to other chemotherapeutics have been diagnosed.

"Treatment" in the meaning of the present invention comprises inhibition of the disease, that means suppressing, reducing or retarding disease progress or its remission or at least one of its clinical symptoms.

"Therapeutically effective dose" of the active substance means the amount of compound which given to patient to cure his state, disorder or disease is sufficient to the curing. "Therapeutically effective dose" may differ, depending on the specific compound used, route of administration, type of disease and its progress, individual response to therapy, as well as the age, body weight, medical condition and sensitivity of treated person, and it may be established by a clinician, based on his knowledge and on clinical trials.

The daily dose may be administered to the patient as a single unit dose once daily or divided into several daily doses in determined time intervals.

The therapeutic daily dose of anthrapyridazone of formula (I) may be administered to the patient as a single unit dose once daily or divided into several daily doses in determined time intervals, e.g. two, three, four or more times per day.

Pharmaceutical preparations, beside the active substance, may contain pharmaceutically acceptable carriers and/or excipients appropriate for a given pharmaceutical form, not having their own pharmacological action and adverse reactions with the active substance.

The pharmaceutical combination according to the present invention, may be formulated in the pharmaceutical form acceptable for systemic administration, for example orally, such as tablets, capsules, film-coated tablets, enteric coated tablets; in the form acceptable for parenteral use, such as solutions, suspensions or lyophilisate for reconstitution ex tempore; or in the form for local administration. The selection and amount of carriers and excipients depends on the form and route of administration of the agent. The appropriate drug form may be formulated with use of techniques well known to those skilled in the art, using any pharmaceutically carriers, solvents, fillers and other excipients.

A pharmaceutical preparation for oral administration may specially be in the form of capsules. In this case, the active substance is combined with a carrier and gelatin capsules are filled with the obtained composition. Capsule filling is in the form of oil solution, suspension or emulsion. Appropriate carriers include, for example castor, coconut, olive, palm, corn, peanut oil, synthetic and natural triglycerides of fatty acids, unsaturated medium-chain fatty acids, modified long-chain fatty acids, glycol esters, polyethylene glycols and others. Appropriate excipients are tensides, for example lecithine, mono- and diglycerides and esters of polyoxyethylenesorbitan.

Capsules may be soft and hard gelatin capsules, differing by composition of gelatin shell for its preparation. Gelatin shell in case of soft capsules include plasticizers, such as glycerol, sorbitol; preservatives, such as benzoic acid and its salts, alkyl hydroxybenzoates; colourants and flavourings.

Pharmaceutical formulation for parenteral administration may be in the form of suspension ready to use, lyophilisate form for reconstitution ex tempore or a concentrate for preparation of intravenous infusions. Carriers appropriate for intravenous pharmaceutical formulations include, for example, sterile aqueous solutions, such as saline solution, carbohydrate solution, for example glucose, mannitol, dextrose lactose and aqueous solutions of buffers, for example phosphate buffer. Moreover, the agent may contain other excipients, conventionally used in order to ensure osmolarity, antioxidants, preservatives and others.

Biological Activity

Biological activity of anthrapyridazone derivatives of formula (I) against multidrug resistant tumor cells including cell lines with overexpression of various exporting protein pumps, MDR-1, BCRP and MRP and broad spectrum resistant cell lines derived from various tissues and organs, was evaluated in the following tests.

Tables 3 and 4 show cytostatic activity in vitro of 2,6-disubstituted and 2- or 6-monosubstituted (Tab.3), and of 2,5-disubstituted-(Tab.-4) tetracyclic anthrapyridazone derivatives using leukemia cell line HL-60 and the resistant cell sublines with resistance induced by vincristine (MDR-1) or doxorubicin (MRP). Activity of compounds is differentiated depending on their structure, but in all cases resistance indexes are more advantageous in comparison with reference compounds: doxorubicin and mitoxantrone.

TABLE 3

Cytostatic activity ($IC_{50}$) in vitro of 2-, 6- and 2- or 6- substituted anthrapyridazone derivatives towards human promyelocytic leukemia cell line HL-60 and resistant sublines HL60/VIN and HL60/DX, vs. Doxorubicin and Mitoxantrone.

| Compound | HL60 $IC_{50}$ [nM] | HL60/VINC $IC_{50}$ [nM] | RI | HL60/DX $IC_{50}$ [nM] | RI |
|---|---|---|---|---|---|
| BS-154 | 0.9 ± 0.1 | 8.1 ± 1.0 | 9.0 | 375 ± 41 | 416.7 |
| BS-121 | 1.3 ± 0.1 | 14.2 ± 1.7 | 10.9 | 564 ± 72 | 433.8 |
| PDZ-3 | 269 ± 41 | 509 ± 54 | 1.9 | 919 ± 89 | 3.4 |
| PDZ-4 | 2085 ± 169 | 2552 ± 286 | 1.2 | 4715 ± 389 | 2.3 |
| PDZ-5 | 382 ± 56 | 677 ± 29 | 1.8 | 1357 ± 135 | 3.6 |
| PDZ-7 | 21 ± 1 | 43 ± 2 | 2.0 | 620 ± 62 | 29.5 |
| PDZ-8 | 719 ± 27 | 850 ± 93 | 1.2 | 4799 ± 1333 | 6.7 |
| PDZ-9 | 311 ± 54 | 574 ± 12 | 1.8 | 1177 ± 94 | 3.8 |
| PDZ-10 | 758 ± 115 | 1156 ± 93 | 1.5 | 2774 ± 494 | 3.7 |
| PDZ-12 | 113 ± 7 | 947 ± 111 | 8.4 | 2682 ± 768 | 23.7 |
| PDZ-13 | 13 ± 1 | 421 ± 24 | 32.4 | 3240 ± 558 | 249.2 |
| PDZ-14 | 28 ± 6 | 79 ± 7 | 2.8 | 870 ± 173 | 31.1 |
| PDZ-15 | 213 ± 64 | 489 ± 68 | 2.3 | 3062 ± 992 | 14.4 |
| PDZ-17 | 98 ± 19 | 477 ± 39 | 4.9 | 2869 ± 447 | 29.3 |
| PDZ-18 | 115 ± 3 | 597 ± 16 | 5.2 | 3497 ± 752 | 30.4 |
| PDZ-20 | 8.6 ± 0.9 | 82.2 ± 6.1 | 9.6 | 2599 ± 436 | 302.2 |
| C-123 | 8.7 ± 0.5 | 58 ± 6 | 6.7 | 827 ± 145 | 95.1 |
| C-131 | 1154 ± 244 | 1010 ± 51 | 0.9 | 4473 ± 428 | 3.9 |
| C-155 | 19 ± 4 | 116 ± 28 | 6.1 | 446 ± 100 | 23.5 |

TABLE 3-continued

Cytostatic activity (IC$_{50}$) in vitro of 2-, 6- and 2- or 6- substituted anthrapyridazone derivatives towards human promyelocytic leukemia cell line HL-60 and resistant sublines HL60/VIN and HL60/DX, vs. Doxorubicin and Mitoxantrone.

| Compound | HL60 IC$_{50}$ [nM] | HL60/VINC IC$_{50}$ [nM] | RI | HL60/DX IC$_{50}$ [nM] | RI |
|---|---|---|---|---|---|
| C-163 | 31 ± 6 | 48 ± 7 | 1.5 | 330 ± 17 | 10.6 |
| C-165 | 2.1 ± 0.4 | 30.8 ± 4.0 | 14.7 | 706 ± 57 | 336.2 |
| C-167 | 111 ± 27 | 393 ± 45 | 3.5 | 1236 ± 206 | 11.1 |
| C-180 | 2.2 ± 0.1 | 8.7 ± 0.4 | 4.0 | 364 ± 36 | 165.5 |
| CP-4 | 2.1 ± 1 | 43 ± 2 | 2.0 | 620 ± 62 | 29.5 |
| Doxorubicin | 16 ± 1 | 882 ± 68 | 55.1 | 9484 ± 1297 | 592.8 |
| Mitoxantrone | 2.1 ± 0.2 | 65.7 ± 6.7 | 31.3 | 3431 ± 661 | 1633.8 |

IC$_{50}$—the concentration of compound that effect 50% inhibition of cell growth after 72 h continuous exposure [nM]
RI—resistance index [IC$_{50(resistant\ cells)}$/IC$_{50(sensitive\ cells)}$]

TABLE 4

Cytostatic activity (IC$_{50}$) in vitro of 2,5-substituted anthrapyridazone derivatives towards human promyelocytie leukemia cell line HL-60 and resistant sublines HL60/VIN and HL60/DX vs. Doxorubicin.

| Compound | HL60 IC$_{50}$ [nM] | HL60VINC IC$_{50}$ [nM] | RI | HL60/DX IC$_{50}$ [nM] | RI |
|---|---|---|---|---|---|
| C-169 | 238.3 ± 24 | 117.8 ± 12 | 0.5 | 328.5 ± 28 | 1.5 |
| C-170 | 8.2 ± 1 | 209.8 ± 52 | 25.6 | 753.4 ± 29 | 91.9 |
| C-171 | 398.1 ± 25 | 374.8 ± 18 | 0.9 | 564.4 ± 34 | 1.4 |
| Doxorubicin | 9.5 ± 2 | 734 ± 72 | 77.3 | 1858.9 ± 143 | 195.7 |

IC$_{50}$—the concentration of compound that effect 50% inhibition of cell growth after 96 h continuous exposure [nM]
RI—resistance index [IC$_{50(resistant\ cells)}$/IC$_{50(sensitive\ cells)}$]

Table 5 presents activity in vitro of anthrapiridazone derivatives towards three cell lines of prostate cancer, naturally multidrug resistant, in comparison with references doxorubicin, mitoxantrone and taxol.

Compounds BS-154 and BS-121 are most active, particularly in comparison with doxorubicin.

TABLE 5

Cytostatic activity (IC$_{50}$) in vitro of anthrapyridazone derivatives towards human prostate cancer cell lines DU154, LNCaP and PC3, vs. Doxorubicin, Mitoxantrone and Taxol.

| Compound | DU145 IC$_{50}$ [nM] | LNCaP IC$_{50}$ [nM] | PC3 IC$_{50}$ [nM] |
|---|---|---|---|
| BS-154 | 3.0 ± 0.7 | 2.6 ± 0.3 | 14.0 ± 3.3 |
| BS-121 | 11.3 ± 2.6 | 5.5 ± 0.7 | 37.6 ± 8.1 |
| PDZ-3 | 725 ± 121 | 549 ± 85 | 709 ± 163 |
| PDZ-4 | 3275 ± 355 | 2789 ± 276 | 5109 ± 206 |
| PDZ-5 | 538 ± 45 | 474 ± 76 | 886 ± 170 |
| PDZ-7 | 28.6 ± 2.8 | 65.4 ± 7.4 | 80.5 ± 12.0 |
| PDZ-8 | 1223 ± 142 | 683 ± 17 | 1713 ± 125 |
| PDZ-9 | 558 ± 129 | 427 ± 80 | 1250 ± 206 |
| PDZ-10 | 2092 ± 583 | 1546 ± 363 | 3010 ± 264 |
| PDZ-12 | 169 ± 47 | 237 ± 45 | 947 ± 37 |
| PDZ-13 | 36.7 ± 7.4 | 50.7 ± 10.2 | 105.8 ± 5.7 |
| PDZ-14 | 32.8 ± 1.4 | 44.8 ± 5.6 | 85.5 ± 10.1 |
| PDZ-15 | 462 ± 52 | 323 ± 34 | 963 ± 171 |
| PDZ-17 | 344 ± 43 | 166 ± 40 | 606 ± 38 |
| PDZ-18 | 418 ± 58 | 465 ± 121 | 974 ± 159 |
| PDZ-20 | 47.3 ± 11.5 | 31.4 ± 4.6 | 244.9 ± 36.0 |
| C-123 | 25.6 ± 2.6 | 52.9 ± 12.1 | 127.3 ± 38.6 |
| C-131 | 1476 ± 127 | 927 ± 92 | 2833 ± 234 |
| C-155 | 71.4 ± 21.6 | 26.2 ± 7.2 | 143.8 ± 32.7 |
| C-163 | 21.8 ± 4.7 | 28.2 ± 7.4 | 122.1 ± 27.6 |
| C-165 | 14.3 ± 3.3 | 8.1 ± 1.0 | 51.6 ± 12.4 |
| C-167 | 294 ± 53 | 202 ± 35 | 776 ± 45 |
| C-180 | 22.6 ± 5.2 | 11.0 ± 1.4 | 75.2 ± 16.2 |
| Doxorubicin | 38.0 ± 7.6 | 22.4 ± 1.9 | 106.1 ± 7.0 |
| Mitoxantrone | 8.5 ± 1.5 | 7.4 ± 1.1 | 18.6 ± 3.8 |
| Taxol | 3.9 ± 0.6 | 1.2 ± 0.3 | 4.0 ± 0.4 |

IC$_{50}$—the concentration of compound that effect 50% inhibition of cell growth after 72 h continuous exposure [nM]

Table 6 presents activity in vitro of selected most active anthrapyridazone derivatives according to the invention against sensitive and multidrug resistant cell line of human breast cancer with exporting MDR-1 protein. It should be mentioned that resistance index is above one order of magnitude better in comparison with doxorubicin and mitoxantrone.

TABLE 6

Cytostatic activity (IC$_{50}$) in vitro of selected anthrapyridazone derivatives against human breast cancer cell line MCF3 and subline MCF7/DX vs. Doxorubicin and Mitoxantrone.

| Compound | MCF7 IC$_{50}$ [nM] | MCF7/DX IC$_{50}$ [nM] | RI |
|---|---|---|---|
| BS-154 | 8.8 ± 0.6 | 8.7 ± 1.2 | 1.0 |
| BS-121 | 39.6 ± 0.8 | 45.3 ± 8.1 | 1.1 |
| Doxorubicin | 19.0 ± 3.3 | 932 ± 145 | 49.1 |
| Mitoxantrone | 7.4 ± 1.9 | 471 ± 160 | 63.6 |

IC$_{50}$—the concentration of compound that effect 50% inhibition of cell growth after 72 h continuous exposure [nM]
RI—resistance index [IC$_{50(resistant\ cells)}$/IC$_{50(sensitive\ cells)}$]

Table 7 presents activity in vitro of selected anthrapyridazone derivatives according to the invention towards sensitive and resistant (MDR-1 type) cell line of human colon adenocarcinoma with resistance induced by mitoxantrone. Tested compounds are considerably more active, in comparison with reference compound mitoxantrone.

TABLE 7

Cytostatic activity (IC$_{50}$) in vitro of selected anthrapyridazone derivatives towards cell lines of human colon adenocarcinoma HT29 and resistant subline HT29/MIT vs. Doxorubicin and Mitoxantrone.

| Compound | HT29 IC$_{50}$ [nM] | HT29/MIT IC$_{50}$ [nM] | RI |
|---|---|---|---|
| BS-154 | 5.2 ± 1.3 | 11.2 ± 2.2 | 2.1 |
| BS-121 | 9.7 ± 1.0 | 39.4 ± 4.3 | 4.1 |
| Doxorubicin | 64.5 ± 19.2 | 97.1 ± 20.9 | 1.5 |
| Mitoxantrone | 11.4 ± 3.9 | 854.2 ± 157.9 | 74.9 |

IC$_{50}$—the concentration of compound that effect 50% inhibition of cell growth after 72 h continuous exposure [nM]
RI—resistance index [IC50$_{(resistant\ cells)}$/IC$_{50(sensitive\ cells)}$]

Tables 8A and 8B present cytostatic activity in vitro of selected anthrapyridazone derivatives according to the invention against panel of sensitive and resistant cell lines, in comparison with doxorubicin, cisplatine and mitoxantrone. These results evidence good activity of tested compound against multidrug resistant cells.

TABLE 8

Cytostatic activity and resistance indexes of compound BS-154 towards cells lines: lymphoblastic leukemia CCRF-CEM and resistant to camptotecine CEM/C2, promyelolytic leukemia HL-60 and its subline resistant to mitoxantrone HL60/MX2, uterus cancer MES-SA and subline resistant to doxorubicin MES-SA/DX5, colon cancer LoVo and subline resistant to doxorubicin line LoVo/DX, vs. Doxorubicin, Cisplatine and Mitoxantrone.

A) Cytostatic activity

| Cell line | IC$_{50}$ [mcg/ml] | | | |
|---|---|---|---|---|
| | BS-154 | Doxorubicin | Cisplatina | Mitoxantrone |
| MES-SA | 0.01333 ± 0.00238 | 0.0705 ± 0.0137 | 2.26 ± 0.58 | 0.23 ± 0.121 |
| MES-SA/DX5 | 0.03833 ± 0.01136 | 13.59 ± 4.97 | 3.29 ± 0.15 | 0.66 ± 0.059 |
| LoVo | 0.00153 ± 0.00102 | 0.2244 ± 0.1860 | 1.59 ± 0.31 | 0.22 ± 0.067 |
| LoVo/DX | 0.06842 ± 0.01273 | 12.07 ± 3.98 | 2.51 ± 0.38 | 2.09 ± 0.519 |
| CCRF-CEM | 0.00373 ± 0.00193 | ND | 1.44 ± 0.49 | 0.0025 ± 0.0010 |
| CEM/C2 | 0.00124 ± 0.00137 | ND | 0.44 ± 0.19 | 0.0028 ± 0.0016 |
| HL60 | 0.00111 ± 0.00002 | ND | 0.22 ± 0.12 | 0.0083 ± 0.0077 |
| HL60/MX2 | 0.00545 ± 0.00304 | ND | 0.56 ± 0.30 | 0.356 |

B) Resistance indexes (RI)

| Cell line | RI | | | |
|---|---|---|---|---|
| | BS-154 | Doxorubicin | Cisplatine | Mitoxantrone |
| MES-SA MES-SA/DX5 | 2.9 | 181.2 | 1.5 | 2.9 |
| LoVo LoVo/DX | 44.7 | 54.7 | 1.6 | 9.5 |
| CCRF-CEM CEM/C2 | 0.3 | ND | 0.3 | 1.1 |
| HL60 HL60/MX2 | 4.9 | ND | 2.5 | 42.9 |

ND—not determined
IC$_{50}$—the concentration of compound that effect 50% inhibition of cell growth after 72 h continuous exposure [mcg/ml]
RI—resistance index [IC$_{50(resistant\ cells)}$/IC$_{50(sensitive\ cells)}$]

Results presented in Table 9 and illustrated on FIG. 1 suggest that compounds according to the invention, similarly to the other synthetic and natural anthraquinone analogs and derivatives, form complexes with DNA with variable stability depending on their structure. It could be supposed that this property explains cytostatic activity of compounds. In Table 9 there are presented quantitative data on the affinity to DNA of tested compounds using the fluorescence method and competitive affinity to DNA of bromine ethydine and tested compounds.

TABLE 9

Interaction of tested compounds with isolated CT-DNA.

| Compound | IC$_{50}$ ± SEM [µM] | K$_{app}$ [×10$^{-7}$M$^{-1}$] |
|---|---|---|
| BS-154 | 0.29 ± 0.01 | 4.28 |
| BS-121 | 0.26 ± 0.02 | 4.83 |
| PDZ-3 | 1.76 ± 0.12 | 0.71 |
| PDZ-4 | 16.83 ± 0.41 | 0.07 |
| PDZ-5 | 1.69 ± 0.10 | 0.75 |
| PDZ-7 | 1.85 ± 0.16 | 0.68 |
| PDZ-8 | 7.29 ± 0.28 | 0.17 |
| PDZ-9 | 2.10 ± 0.10 | 0.60 |
| PDZ-10 | 3.15 ± 0.15 | 0.40 |
| PDZ-12 | 2.64 ± 0.29 | 0.48 |
| PDZ-13 | 1.84 ± 0.16 | 0.68 |
| PDZ-14 | 0.99 ± 0.01 | 1.27 |
| PDZ-15 | 3.08 ± 0.19 | 0.41 |
| PDZ-17 | 0.46 ± 0.08 | 2.72 |
| PDZ-18 | 1.96 ± 0.12 | 0.64 |
| PDZ-20 | 0.22 ± 0.06 | 5.79 |
| C-123 | 0.31 ± 0.04 | 4.04 |
| C-131 | 1.63 ± 0.12 | 0.77 |
| C-155 | 0.31 ± 0.01 | 4.02 |
| C-163 | 0.23 ± 0.01 | 5.57 |
| C-165 | 0.37 ± 0.08 | 3.44 |
| C-167 | 2.04 ± 0.07 | 0.62 |
| C-180 | 0.28 ± 0.05 | 4.53 |
| Idarubicin | 0.50 ± 0.06 | 2.50 |
| Doxorubicin | 0.08 | 15.00 |
| Ametantrone | 0.049 ± 0.006 | 25.66 |
| Mitoxantrone | 0.048 ± 0.004 | 26.13 |

IC$_{50}$—the concentration of compound that effect 50% decrease in fluorescence intensity of DNA-bromide ethydine complex [µM]
K$_{app}$ [×10$^{-7}$M$^{-1}$]—relative constant of DNA-compound bonding; K$_{app}$ = (1.26/C$_{50}$) × K$_{EtBr}$ where K$_{EtBr}$ = 10$^{7}$M; 1.26 (µM)—the concentration of EtBr in complex with DNA FIG. 1 below illustrates molecular structure of exemplary intercalating complex of compound BS-121 with DNA, calculated by molecular modeling methods.

The calculation have been done using GROMACS 3.3.1 software package with the use of power field GROMOS96 43a1. Initial geometries of compounds molecules were obtained using PRODRG program. Next, they were introduced to library data of GROMACS. Employing rungms01 program, molecules topology files have been obtained. The molecules were placed in cubic box in such manner that distance of atoms from box walls was not smaller than 0.9 nm. Box was filled with water molecules using genbox program. Tested molecules were hydrochlorides, in the next step the charges were equilibrated, applying genion program.

Figure 2:
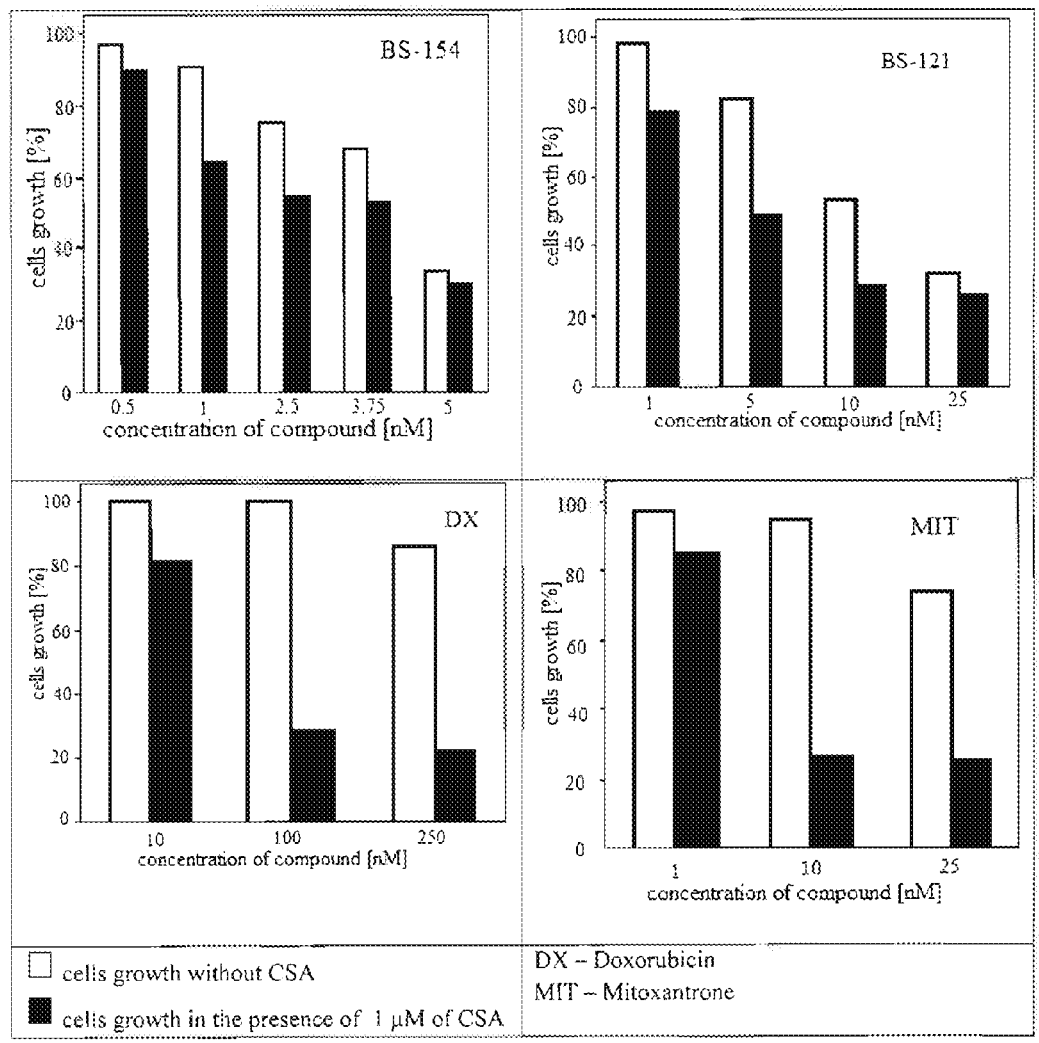
FIG. 2 shoes experimentally determined substrate properties of selected antgraoyridazone derivatives vs. Doxorubicin and Mitroxantrone. Activity in vitro against human promyelacytic leykemia cell line HL60/VINC in the presence of cyclosporine A (MDR-1 pump inhibitor).
Figure 3:
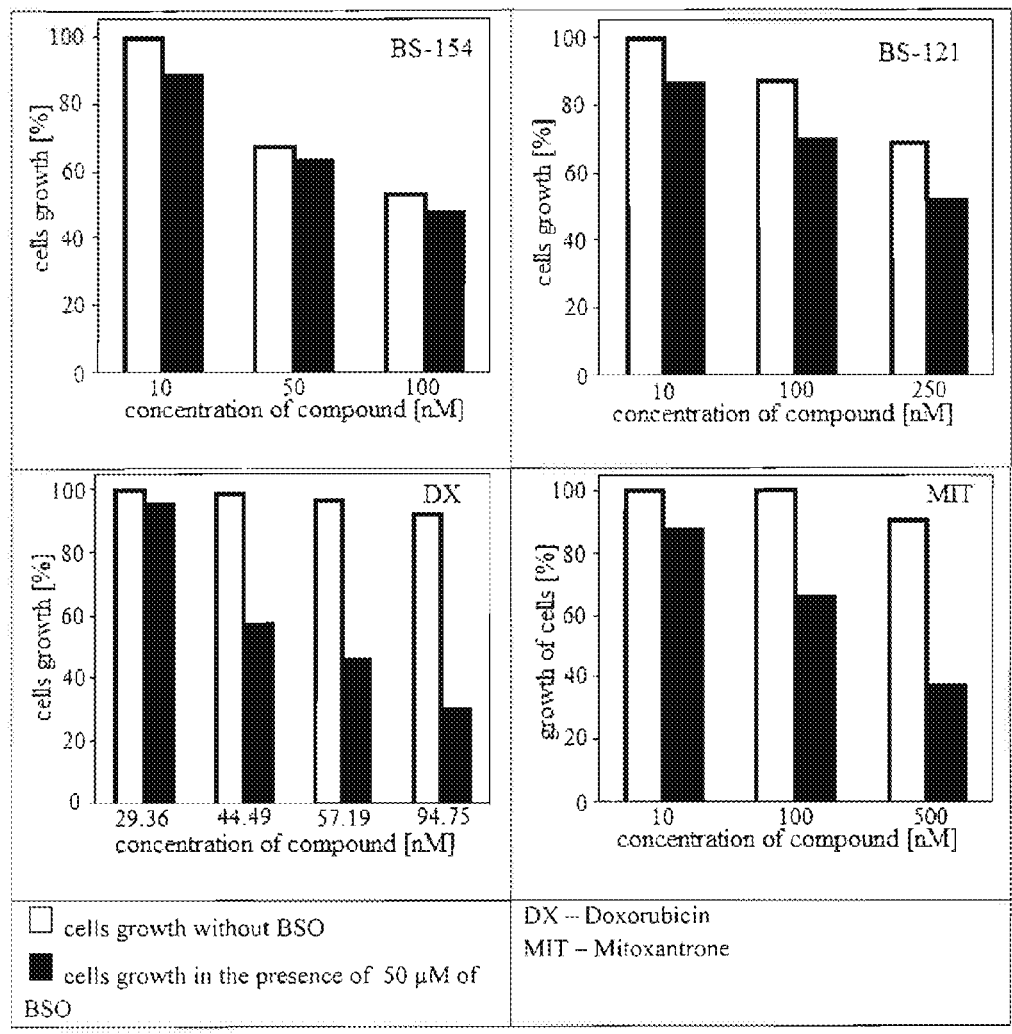
FIG. 3 shows experimentally determined substrate properties of selected anhthapyridazone derivatives vs. Doxorubicin and Mitroxantrone. Activity in vitro against human promyelolytic leukemia HL60/DX in the presence of D-L-buthionine-(S,R)-sulphoximine (BSO), MRP pump inhibitor.

FIG. 2 and FIG. 3 show, on exemplary compounds BS-154 and BS-121, the results of experiments indicating that anthrapyridazone derivatives of the invention exhibit cytostatic effect on multidrug resistant cells because they are poor substrates for exporting pumps. FIG. 2 proves that blocking MDR-1 pump function with the aid of an inhibitor cyclosporine A (CSA) does not essentially affect the cytostatic activity of compounds BS-154 and BS-121, however, has positive influence on maintaining the cytostatic activity of doxorubicin and mitoxantrone, which are good substrates of this pomp. Similarly, FIG. 3 shows data concerning these compounds and MRP pump.

Obtained data indicate that both exemplary compounds are poor substrates for MDR pump unlike doxorubicin and mitoxantrone.

Presence of MRP protein inhibitor essentially influences the cytostatic activity of Doxorubicin and Mitoxantrone, while only partially of BS-154 and BS-121 activity.

Figure 4:
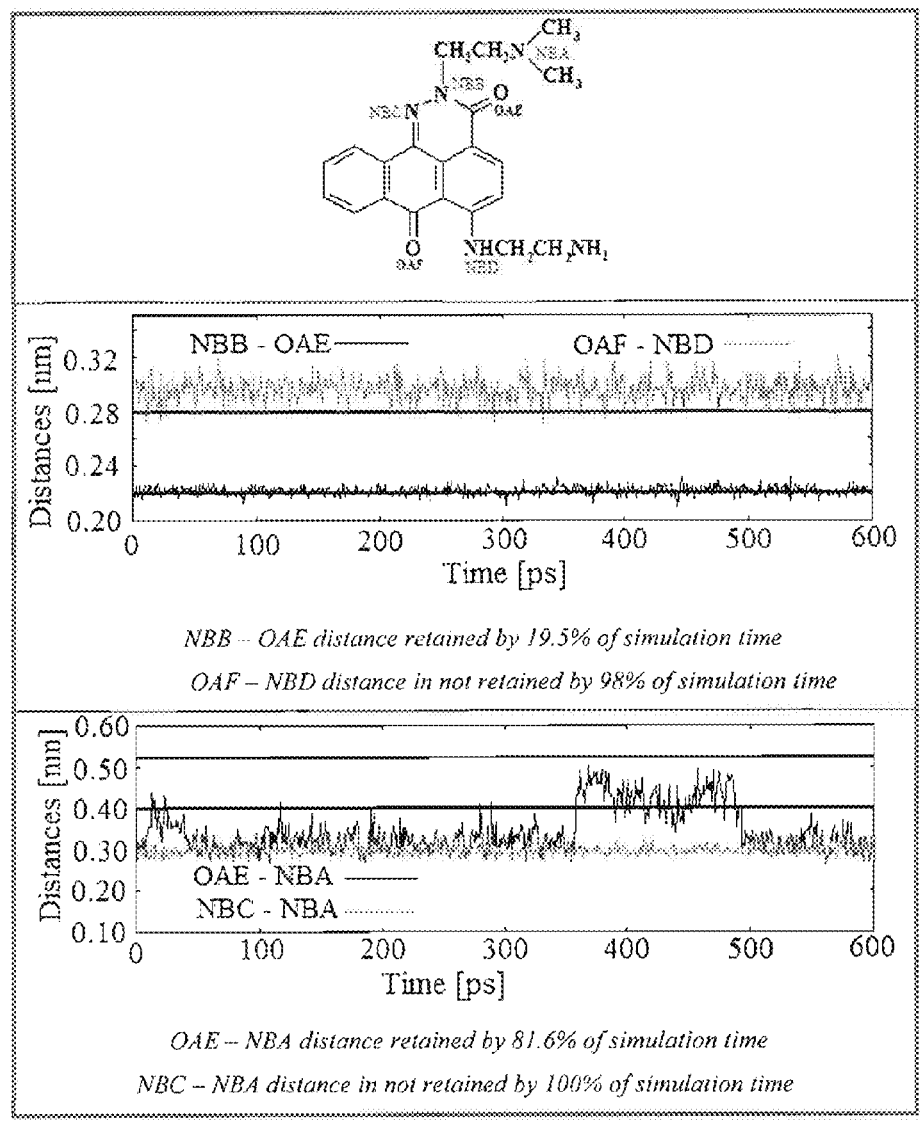
FIG. 4 shows substrate properties of compound BS-121 for MDR-1 protein determined by molecular modeling methods.

Poor substrate properties of compounds according to the invention towards exporting pumps were also confirmed, on the example of compound BS-121 (FIG. 4) basing on the use of molecular modeling method. The calculations were based on the analysis of spacial distribution and distances between molecule atoms, which can be electron donors for the formation of hydrogen bonds with MDR-1 protein, indispensable for the recognition of its substrate by that protein (A. Seeling, Eur. J. Biochem., 251, 252, 1998). Molecule of compound BS-121 analyzed by that method does not fulfill necessary terms, so can not be a substrate that exporting protein.

Changes of distances between atoms which could be electron donors for hydrogen bonds with MDR-1 transporter measured during 600 ps indicate that these distances are beyond the range indispensable for MDR-1 transporter substrate.

The invention is further illustrated by the following non-limiting examples.

EXAMPLES

Example 1 and 24 describe methods of substrates synthesis for appropriate compounds.

In Examples 2-23 and 25-29 the synthesis of compounds according to the invention is described.

Examples 2-23 describe the synthesis of tetracyclic 2,6-di and 2-monosubstituted derivatives, Examples 25-27 describe the synthesis of 1,5-disubstituted derivatives, while examples 28 and 29 describe synthesis of pentacyclic 2,6- or 2,7-disubstituted derivatives. Structures of new tetra- and pentacyclic compounds, described in examples, are shown in Tab. 1 and 2.

Example 1

2-[2-(Dimethylamino)ethyl]-6-chloro-2,7-dihydro-3H-dibenzo[de,h]cynnoline-3,7-dione A suspension of 1-chloro-4-methylanthraquinone (6 g, 23.37 mmol) in the mixture of 12 ml 65% nitric acid and 24 ml of water is heated in the pressure reactor with teflon lining at 200° C. for 6 hours. The reaction mixture, after cooling, is diluted with water and the resulting precipitate is filtrated. The obtained crude acid is treated with chloroform, filtered and next crystallized with ethyl acetate to give 4.1 g (61% yield) of 4-chloroanthra quinone 1-carboxylic acid.

$^1$H NMR (acetone, 200 MHz) δ 7.46 (d, 1H, J=8.4 Hz); 7.91 (m, 2H); 7.98 (d, 1H, J=8.4 Hz); 8.26 (m, 2H). MS-FAB m/z (relative intensity, %): 285([M]$^+$, 100%).

To a suspension of 4-chloroanthraquinone-1-carboxylic acid (2.5 g, 8.74 mmol) in 30 ml of toluene 2.2 g of phosphorus pentachloride is added and the reaction mixture is stirred for 30 minutes to obtain clear solution. Next, to the solution, 1.5 ml of triethylamine is added and after then 2.25 g (21.8 mmol) of 2-(dimethylamino)ethylhydrazine in 59 ml of toluene is added dropwise. The reaction mixture is stirred for 90 minutes, the obtained solid is filtered, washed with toluene (2×10 ml) and dissolved in 200 ml chloroform. The solution is twice washed with 5% solution of $Na_2CO_3$ (2×60 ml) and water (2×50 ml). The organic layer is dried over anhydrous sodium sulfate and the solvent is evaporated under reduced pressure. The residue is purified by column chromatography (Silica Gel) in chloroform-methanol (80:1) solvent system to afford 0.96 g (31% yield) of 2-[2-(dimethylamino)ethyl]-6-chloro-2,7-dihydro-3H-dibenzo[de,h]cynnoline-3,7dione $^1$H NMR (CDCl$_3$, 200 MHz) δ2.37 (s, 6H, CH$_3$); 2.89 (t, 2H, J=6.6 Hz); 4.53 (t, 2H, J=6.6 Hz); 7.64 (dd, 1H, J$_1$=7.7 Hz, J$_2$=1.5 Hz); 7.76 (dd, 1H, J$_1$=7.7 Hz, J$_2$=1.5 Hz); 7.95 (d, 1H, J=8.4 Hz); 8.38 (dd, 1H, J$_1$=7.7 Hz, J$_2$=1.1 Hz); 8.48 (dd, 1H, J$_1$=7.7 Hz, J$_2$=1.5 Hz); 8.61 (d, 1H, J=8.4 Hz)

Example 2

2-[2-(Dimethyloamino)ethyl]-6-{[2-(methylamino)ethyl]amino}-2,7-dihydro-3H-dibenzo[de,h]cynnoline-3,7-dione (BS-154), dihydrochloride Solution of 50 mg (0.14 mmol) of 2-[2-(dimethylamino)ethylo]-6-chloro-2,7-dihydro-3H-dibenzo[de,h]cynnoline-3,7-dione and 1 ml of N-methylethylenediamine in 2 ml of pyridine is stirred at 60° C. for 30 minutes under nitrogen atmosphere. The progress of the reaction is monitored by thin layer chromatography on Silica Gel 60 (Merck) in chloroform-methanol (5:1) solvent system. The reaction mixture is diluted with chloroform and, to remove excess of amine, is carefully washed with diluted solution of hydrochloric acid and next with water. The organic layer is dried over anhydrous sodium sulphate, the solvent is evaporated under reduced pressure. The residue is purified by column chromatography (Silica gel, Merck, –200 mesh) in the solvent system successively: chloroform-methanol 10:1; 5:1; chloroform-methanol-25% solution of ammonia 5:1:0.1.

$^1$H NMR (CDCl$_3$) δ=2.37 (s, 6H); 2.57 (s, 3H); 2.88 (t, 2H, J=6.8 Hz); 3.06 (t, 2H, J=5.8 Hz); 3.62 (q, 2H, J=5.8 Hz); 4.50 (t, 2H, J=6.7 Hz); 7.25 (d, 1H, J=9.3 Hz); 7.59-7.72 (m, 2H); 8.35-8.49 (m, 3H); 10.96 (t, 1H, J=4.7 Hz). MS-FAB m/z (relative intensity,%): 392 ([M+1]$^+$, 100).

2-[2-(Dimethylamino)ethyl]-6-{[2-(methylamino)ethyl]amino}-2,7-dihydro-3-H-dibenzo[de,h]cynnoline-3,7-dione is converted into its dihydrochloride as follows: to the solution of compound in the mixture of chloroform-methanol, at temperature 5° C. a slightly molar excess of hydrogen chloride in absolute ethyl ether is added dropwise. The yellow-orange solid precipitated by anhydrous ethyl ether is separated and crystalizated with the mixture of methanol-ethyl ether. The product is obtained with final yield 45%, melting point 272-274° C. (with decomposition).

Example 3

2-[2-(Dimethylamino)ethyl]-6-[2-(aminoethyl)amino)-2,7-dihydro-3H-dibenzo[de,h]cynnoline-3,7-dione (BS-121), dihydrochloride Solution of 50 mg (0.14 mmol) of 2-[2-(dimethylamino)ethyl]-6-chloro-2,7-dihydro-3H-dibenzo[de,h]cynnoline-3,7-dione and 0.5 ml of 1,2-diaminoethane in 1 ml of pyridine is stirred at 80° C. for 1 hour under nitrogen atmosphere. The progress of the reaction is monitored by thin layer chromatography as in Example 2 in chloroform-methanol-25% solution of ammonia (5:1:0.1) solvent system. Subsequent procedure is analogous to that described in Example 2. 2-[2-(Dimethylamino)ethyl]-6-[2-(aminoethyl)amino)-2,7-dihydro-3H-dibenzo[de,h]cynnoline-3,7-dione (BS-121) is isolated on column chromatography as described in Example 2 in the solvent system, successively: chloroform-methanol 50:1; 20:1; 10:1; 5:1, then chloroform methanol-25% solution of ammonia 5:1:0.1.

The compound is converted into its dihydrochloride as described in Example 2. Yellow powder is obtained with the yield 55%, melting point 280-282° C.

$^1$H NMR (d$_6$-DMSO) δ=2.21 (s, 6H); 2.72 (t, 2H, J=6.3 Hz); 2.88 (t, 2H, J=5.8 Hz); 3.44 (q, 2H, J=5.9 Hz); 4.33 (t, 2H, J=6.8 Hz); 7.37 (t, 1H, J=9.3 Hz); 7.65 (t, 1H, J=7.4 Hz); 7.76 (t, 1H, J=7.6 Hz); 8.16 (d, 1H, J=9.4 Hz); 8.20 (d, 1H,

J=7.8 Hz); 8.34 (d, 1H, J=7.8 Hz); 10.80 (t, 1H, J=4.8 Hz). MS-FAB m/z (relative intensity, %): 378 ([M+1]⁺, 100)

Example 4

2-[2-(Dimethylamino)ethyl]-6-(N-methylamino)-2,7-dihydro-3H-dibenzo[de,h]cynnoline-3,7-dione (PDZ-7), hydrochloride To the solution of 100 mg (0.28 mmol) of 2-[2-(dimethylamino)ethylo]-6-chloro-2,7-dihydro-3H-dibenzo[de,h]cynnoline-3,7-dione in 20 ml ethanol, 90 mg of N-methylamine hydrochloride and 2 ml of N,N,N-triethylamine are added. The reaction mixture is heated at 80-90° C. for 2 hours. Progress of the reaction is monitored as described in Example 2. Next, the reaction mixture is evaporated under reduced pressure, diluted with chloroform and washed with water. The organic layer is dried over anhydrous sodium sulfate and the solvent is evaporated under reduced pressure.

2-[2-(Dimethylamino)ethyl]-6-(N-methylamino)-2,7-dihydro-3H-dibenzo[de,h]cynnoline-3,7-dione (PDZ-7) is isolated on column chromatography as described in Example 2 in the solvent system: chloroform-methanol 10:1, then 2:1.

¹H NMR (CDCl₃) δ=2.87 (s, 6H); 3.12 (d, 3H, J=5.2 Hz); 3.53 (t, 2H, J=6.6 Hz); 4.83 (t, 2H, J=6.6 Hz); 7.13 (d, 1H, J=9.4 Hz); 7.62-7.66 (m, 2H); 8.35-8.45 (m, 2H); 8.49 (d, 1H, J=6.8 Hz); 10.70-10.78 (m, 1H). MS-FAB m/z (relative intensity, %): 348 ([M]⁺· 100).

The compound is converted into its hydrochloride as described in Example 2. Yellow powder is obtained with the yield 50%, melting point 264-266° C. (with decomposition).

Example 5

2-[2-(Dimethylamino)ethyl]-6-{[2-(ethylamino)ethyl]amino}-2,7-dihydro-3H-dibenzo[de,h]cynnoline-3,7dione (C-180), dihydrochloride Solution of 50 mg (0.14 mmol) of 2-[2-(dimethylamino)ethylo]-6-chloro-2,7-dihydro-3H-dibenzo[de,h]cynnoline-3,7dione and 1 ml of N-ethylethylenediamine in 2 ml of pyridine is stirred at 60° C. for 30 minutes under nitrogen atmosphere. Progress of the reaction and subsequent procedure are analogous to that described in Example 2. 2-[2-(Dimethylamino)ethyl]-6-{[2-(ethylamino)ethyl]amino}-2,7-dihydro-3H-dibenzo[de,h]cynnoline-3,7-dione (C-180) is isolated on column chromatography as described in Example 2 in the solvent system chloroform-methanol 5:1.

The compound is converted into its dihydrochloride as described in Example 2. Yellow powder is obtained with the yield 55%, melting point 288-290° C. (with decomposition).

¹H NMR (d₆-DMSO) δ=1.30 (t, 3H, J=7.0 Hz); 2.85 (q, 2H, J=7.0 Hz); 2.89 (s, 6H); 3.32 (q, 2H, J=6.1 Hz); 3.65 (t, 2H, J=5.6 Hz); 3.97 (q, 2H, J=6.2 Hz); 4.70 (t, 2H, J=5.6 Hz); 7.50 (d, 1H, J=9.0 Hz); 7.70-7.90 (m, 2H); 8.20-8.34 (m, 2H); 8.50 (d, 1H, J=8.0 Hz); 9.15 (br. s., 1H, D₂O exchangeable); 10.18 (br. s., 1H, D₂O exchangeable); 10.76 (t, 1H, J=4.8 Hz). MS-FAB m/z (relative intensity, %): 406([M+1]⁺, 100).

Example 6

2-[2-(Dimethylamino)ethyl]-6-[(3-aminopropyl)amino]-2,7-dihydro-3H-dibenzo [de,h]cynnoline-3,7-dione (PDZ-20), dihydrochloride Solution of 50 mg (0.14 mmol) of 2-[2-(dimethylamino)ethylo]-6-chloro-2,7-dihydro-3H-dibenzo[de,h]cynnoline-3,7-dione and 0.5 ml of 1,3-diaminopropane in 1 ml of pyridine is stirred at 104° C. for 3 hours under nitrogen atmosphere. Progress of the reaction progress is monitored as described in Example 3. Subsequent procedure is analogous to that described in Example 2. 2-[2-(Dimethylamino)ethyl]-6-[(3-aminopropyl)amino]-2,7-dihydro-3H-dibenzo[de,h]cynnoline-3,7-dione (PDZ-20) is isolated on column chromatography as described in Example 2 in the solvent system, successively: chloroform-methanol 50:1; 20:1; 10:1, then chloroform-methanol-25% solution of ammonia 5:1:0.1.

¹H NMR (CDCl₃) δ 1.92 (t, 2H, J=6.9 Hz); 2.08 (s, 2H, NH, D₂O exchangeable); 2.34 (s, 6H); 2.80-2.96 (m, 4H); 3.43-3.49 (m, 2H); 4.44 (t, 2H, J=6.9 Hz); 7.12 (d, 1H, J=9.4 Hz); 7.54-7.65 (m, 2H); 8.24-8.41 (m, 3H); 10.70 (t, 1H, J=4.6 Hz). MS-FAB m/z (relative intensity, %): 392 ([M+1]⁺, 100).

The compound is converted into its dihydrochloride as described in Example 2. Yellow powder is obtained with the yield 58%, melting point 149-150° C. (with decomposition).

Example 7

2-[2-(Dimethylamino)ethyl]-6-[(3-acetylaminopropyl)amino]-2,7-dihydro-3H-dibenzo [de,h]cynnoline-3,7-dione (PDZ-13), hydrochloride Solution of 50 mg (0.13 mmol) of 2-[2-(dimethylamino)ethyl]-6-[(3-aminopropyl)amino]-2,7-dihydro-3H-dibenzo[de,h]cynnoline-3,7-dione and 5 ml the mixture of acetic anhydride/pyridine (the ratio 2/1 by volume) is stirred at room temperature for 3 hours. Progress of the reaction is monitored as described in Example 2. Then the reaction mixture is diluted with 15 ml of chloroform and repeatedly washed with 5% solution of Na₂CO₃. The organic layer is dried over anhydrous sodium sulphate, and solvent is evaporated under reduced pressure. 2-[2-(Dimethylamino)ethyl]-6-[(3-acetylaminopropyl)amino]-2,7-dihydro-3H-dibenzo[de,h]cynnoline-3,7-dione (PDZ-13) is isolated on column chromatography as described in Example 2 in the solvent system, successively: chloroform-methanol 30:1; 10:1; 5:1; 2:1.

¹H NMR (CDCl₃) δ 2.0 (t, 2H, J=6.6 Hz); 2.10 (s, 3H); 2.68 (s, 6H); 3.26 (t, 2H, J=6.6Hz); 3.37-3.51 (m, 4H); 4.65 (t, 2H, J=6.7 Hz); 6.55 (t, 1H, J=5.5 Hz, D₂O exchangeable), 6.96 (d, 1H, J=9.2 Hz); 7.54-7.62 (two overlapping triplets, 2H, J=7.41 Hz); 8.13 (d, 1H, J=9.7 Hz); 8.20 (d, 1H, J=7.61 Hz); 8.30 (d,1H, J=7.7 Hz); 10.70 (t, 1H, J=4.7 Hz, D₂O exchangeable). MS-FAB m/z (relative intensity, %): 434 ([M+1]⁺, 100).

The compound is converted into its hydrochloride as described in Example 2. Yellow powder is obtained with the yield 45%, melting temperature is not measured because of its strong hygroscopicity.

Example 8

2-[2-(Dimethylamino)ethyl]-6-(acetylamino)-2,7-dihydro-3H-dibenzo[de,h]cynnoline-3,7-dione (PDZ-14), hydrochloride Solution of 50 mg (0.15 mmol) of 2-[2-(dimethylamino)ethyl]-6amino-2,7-dihydro-3H-dibenzo[de,h]cynnoline-3,7-dione and 5 ml the mixture of acetic anhydride/pyridine (the ratio 2/1 by volume) is stirred at 100° C. for 24 hours. Progress of the reaction is monitored as described in Example 2. Subsequent procedure is identical as in Example 7.

2-[2-(Dimethylamino)ethyl]-6-(acetylamino)-2,7-dihydro-3H-dibenzo[de,h]cynnoline-3,7-dione (PDZ-14) is isolated on column chromatography as described in Example 2 in the solvent system, successively: chloroform-methanol 30:1; 10:1; 5:1.

$^1$H NMR (CDCl$_3$) δ 2.41 (s, 9H); 2.94 (t, 2H, J=6.9 Hz); 4.54 (t, 2H, J=6.8 Hz); 7.69 (t, 1H, J=7.8 Hz); 7.78 (t, 1H, J=8.3 Hz); 8.34 (d, 1H, J=7.8 Hz); 8.49 (d, 1H, J=7.8 Hz); 8.64 (d, 1H, J=9.2 Hz); 9.28 (d, 1H, J=9.8 Hz); 13.1 (s, 1H). MS-FAB m/z (relative intensity, %): 377 ([M+1]$^+$, 100)

The compound is converted into its hydrochloride as described in Example 2. Bright yellow powder is obtained with the yield 20%, melting point 250-253° C.

Example 9

2-[2-(Dimethylamino)ethyl]-6-{[(2-diethylamino)ethyl]amino}-2,7-dihydro-3H-dibenzo[de,h]cynnoline-3,7-dione (C-155), dihydrochloride Solution of 50 mg (0.14 mmol) of 2-[2-(dimethylamino)ethylo]-6-chloro-2,7-dihydro-3H-dibenzo[de,h]cynnoline-3,7-dione and 1 ml of N,N-diethylethylenediamine in 2 ml of pyridine is stirred at 60° C. for 30 minutes under a nitrogen atmosphere. Progress of the reaction and subsequent procedure are analogous to that described in Example 2.

2-[2-(Dimethylamino)ethyl]-6-{[(2-diethylamino)ethyl]amino}-2,7-dihydro-3H-dibenzo[de,h]cynnoline-3,7-dione (C-155) is isolated on column chromatography as described in Example 2 in the solvent system, successively: chloroform-methanol 10:1; 5:1 then chloroform-methanol-25% solution of ammonia 5:1:0.1.

$^1$H NMR (CDCl$_3$) δ=1.15 (t, 6H, J=7.0 Hz); 2.43 (s, 6H), 2.70 (q, 4H, J=7.1 Hz); 2.87-2.99 (m, 4H); 3.61 (q, 2H, J=6.3 Hz); 4.56 (t, 2H, J=6.7 Hz); 7.27 (d, 1H, J=0.9 Hz); 7.57-7.71 (m, 2H); 8.37-8.54 (m, 3H); 10.93 (broad triplet, 1H). MS-FAB m/z (relative intensity, %): 433 ([M]$^+$, 100).

The compound is converted into its dihydrochloride as described in Example 2. Yellow powder is obtained with the yield 56%, melting point 264-266° C.

Example 10

2-[2-(Dimethylamino)ethyl]-6-(N-benzylamino)-2,7-dihydro-3H-dibenzo[de,h]cynnoline-3,7-dione (PDZ-8), hydrochloride Solution of 50 mg (0.14 mmol) of 2-[2-(dimethylamino)ethylo]-6-chloro-2,7-dihydro-3H-dibenzo[de,h]cynnoline-3,7-dione and 0.5 ml of benzylamine in 1 ml of pyridine is stirred at 70-80° C. for 150 minutes under nitrogen atmosphere. Progress of the reaction and subsequent procedure are analogous to that described in Example 2. 2-[2-(Dimethylamino)ethyl]-6-(N-benzylamino)-2,7-dihydro-3H-dibenzo[de,h]-cynnoline-3,7-dione (PDZ-8) is isolated on column chromatography as described in Example 2 in the solvent system chloroform-methanol 5:1. The compound is converted into its hydrochloride as described in Example 2. Yellow-orange powder is obtained with the yield 60%, melting point 232-233° C.

$^1$H NMR (DMSO-d$_6$) δ=2.88 (d, 6H, J=5.4 Hz); 3.10 (t, 2H, J=6.9 Hz); 3.63 (d, 2H, J=6.1 Hz); 4.60 (t, 2H, J=6.9 Hz); 7.24-7.46 (m, 6H); 7.64-7.86 (m, 2H); 8.20 (m, 2H); 8.40 (d, 1H, J=7.8 Hz), 10.30 (broad singlet, 1H); 10.90 (t, 1H, J=4.8 Hz). MS-FAB m/z (relative intensity, %): 424 ([M]$^+$, 100).

Example 11

2-[2-(Dimethylamino)ethyl]-6-[2-(2-aminoethylamino)ethanolo]-2,7-dihydro-3H-dibenzo[de,h]cynnoline-3,7-dione (C-165), dihydrochloride Solution of 70 mg (0.2 mmol) of 2-[2-(dimethylamino)ethylo]-6-chloro-2,7-dihydro-3H-dibenzo[de,h]cynnoline-3,7-dione and 0.2 ml of 2-(2-aminoethylamino) ethanol in 0.7 ml of pyridine is stirred at 55° C. for 90 minutes under nitrogen atmosphere. Progress of the reaction and subsequent procedure are analogous to that described in Example 2.

2-[2-(Dimethylamino)ethyl]-6-[2-(2-aminoethylamino)ethanolo]-2,7-dihydro-3H-dibenzo[de,h]cynnoline-3,7-dione (C-165) is isolated on column chromatography as described in Example 2 in the solvent system, successively: chloroform-methanol 20:1; 10:1; 5:1 then chloroform-methanol-25% solution of ammonia 5:1:0.1.

$^1$H NMR (CDCl$_3$) δ=2.30 (s, 6H); 2.50-2.70 (m, 1H, D$_2$O exchangeable); 2.84 (t, 2H, J=6.9 Hz); 2.94 (t, 2H, J=5.1 Hz); 3.10 (t, 2H, J=5.9 Hz); 3.54 (q, 2H, J=5.9 Hz); 3.75 (t, 2H, J=4.8 Hz); 4.48 (t, 2H, J=6.7 Hz); 7.06 (d, 1H, J=9.4 Hz); 7.50-7.65 (m, 2H); 8.20-8.36 (m,3H); 11.00 (t, 1H, J=4.5 Hz, D$_2$O difficulty exchangeable). MS-FAB m/z (relative intensity, %): 422 ([M+1]$^+$, 100), 376 ([M−45]$^+$, 25).

The compound is converted into its dihydrochloride as described in Example 2. Bright yellow powder is obtained with the yield 55%, melting point 254-255° C.

Example 12

2-[2-(Dimethylamino)ethyl]-6-[(N,N-dimethylacetamido)amino]-2,7-dihydro-3H-dibenzo[de,h]cynnoline-3,7-dione (PDZ-12), hydrochloride Solution of 180 mg (0.5 mmol) of 2-[2-(dimethylamino)ethyl]-6-amino-2,7-dihydro-3H-dibenzo[de,h]cynnoline-3,7-dione and 350 mg (2.5 mmol) of glycine ethyl ester hydrochloride and 0.35 ml of triethylamine in 7.5 ml of pyridine is intensively stirred at 85-90° C. for 30 minutes. Progress of the reaction is monitored as described in Example 2. 2-[2-(Dimethylamino)ethyl]-6-carboethoxymethylamino-2.7-dhydro-3H-dibenzo[de,h]cynnoline-3,7-dione is isolated on column chromatography as described in Example 2 in the solvent system, successively: chloroform-methanol 20:1; 15:1. The yield of the isolated product is 80%.

84 mg (0.2 mmol) of above obtained compound, 4,2 ml of methanol, 39 mg NaCN and excess of dimethylamine (solution in tetrafydrofuran) in a closed flask is stirred at 50° C. for 5 hours. Progress of the reaction is monitored as described in Example 2. The reaction mixture is evaporated under reduced pressure and the residue is dissolved in a mixture of hot chloroform with methanol.

2-[2-(Dimethylamino)ethyl]-6-[(N,N-dimethylacetamido)amino]-2,7-dihydro-3H-dibenzo[de,h]cynnoline-3,7-dione (PDZ-12) is isolated on column chromatography as described in Example 2 in the solvent system: chloroform-methanol 20:1, then 5:1.

$^1$H NMR (CDCl$_3$) δ=2.47 (s, 6H); 3.00 (t, 2H, J=6.7 Hz); 3.09 (s, 3H); 3.10 (s, 3H); 4.15 (d, 2H, J=4.0 Hz); 4.50 (t, 2H, J=6.7 Hz); 6.95 (d, 1H, J=9.3 Hz); 7.50-7.68 (m, 2H); 8.24 (d, 1H; J=9.4 Hz); 8.30-8.38 (m, 2H); 11.20 (m, 1H). MS-FAB: m/z (relative intensity, %): 420 ([M+1]$^+$, 22), 375 ([M−45], 100).

The compound is converted into its hydrochloride as described in Example 2. Yellow powder is obtained with the yield 50%, melting point 267-269° C. (with decomposition).

Example 13

2-[2-(Dimethylamino)propyl]-6-{[2-(dimethylamino)propyl]amino}-2,7-dihydro-3H-dibenzo[de,h]cynnoline-3,7-dione (C-123), dihydrochloride Solution of 50 mg (0.17 mmol) of 2[-2-(dimethylamino)propyl]-6-chloro-2,7-dihydro-3H-dibenzo[de,h]cynnoline-3,7-dione and 1 ml of N,N-dimethyl-1,3-diamino propane in 2 ml of pyridine is stirred at 70° C. for 30 minutes under nitrogen atmosphere. Progress of the reaction and subsequent procedure are analogous to that described in Example 2. 2-[2-(Dimethylamino)propyl]-6-{[2-(dimethylamino) propyl]amino}-2,7-dihydro-3H-dibenzo [de,h]cynnoline-3,7-dione (C-123) is isolated on column chromatography as described in Example 2 in the solvent system, successively: chloroform-methano 10:1; 5:1. The compound is converted into its dihydrochloride as described in Example 2. Yellow powder is obtained with the yield 43%, melting point 292-294° C. (with decomposition).

$^1$H NMR (DMSO-$d_6$) δ=1.80 (t, 2H, J=6.3 Hz); 2.00 (m, 2H); 2.20 (s, 6H); 2.40 (t, 2H, J=6.4 Hz); 2.78 (s, 6H); 3.20 (m, 2H); 3.50 (m, 2H); 4.20 (t, 2H, J=6.5 Hz); 7.68 (d, 1H, J=9.8 Hz); 7.75 (t, 1H, J=7.6 Hz); 7.85 (t, 1H, J=7.6 Hz); 8.10-8.21 (m, 2H); 8.45 (d, 1H, J=7.8 Hz); 10.05 (s, 1H); 10.60 (s, 1H); 10.98 (t, 1H, J=4.8 Hz). MS-FAB m/z (relative intensity, %): 433 ([M]$^+$, 100).

Example 14

2-(2-Morpholinethyl)-6-amino-2,7-dihydro-3H-dibenzo[de,h]cynnoline-3,7-dione (PDZ-4), hydrochloride 286 mg (1 mmol) of 4-chloroanthraquinone-1-carboxylic acid and 286 mg of phosphorus pentachloride in 4 ml anhydrous benzene is stirred at room temperature for 40 minutes. The progress of the reaction is monitored as described in Example 2. The reaction mixture is repeatedly evaporated with anhydrous benzene under reduced pressure, next the precipitate is dissolved with 20 ml of anhydrous benzene and 0.4 ml (3 mmol) of 2-(morpholinethyl) hydrazine in 8 ml of benzene is added dropwise under stirring. The progress of the reaction is monitored as described in Example 2. After 30 minutes the reaction mixture is diluted in chloroform, next washed with 5% solution of Na$_2$CO$_3$ and water. The organic layer is dried over anhydrous sodium sulphate and the solvent is evaporated under reduced pressure. 2-(2-Morpholinethyl)-6-chloro-2,7-dihydro-3H-dibenzo[de,h]cynnoline-3,7-dione is isolated on column chromatography as described in Example 2 in the solvent system: chloroform-methanol 50:1, then 20:1. The yield of the isolated product is 55%.

Solution of 40 mg (0.1 mmol) above obtained compound in 0.4 ml of DMA and 6 ml of methanol saturated with gas ammonia in a closed flask is stirred at 60° C. for 4 hours. The progress of the reaction is monitored as described in Example 3. The reaction mixture is evaporated under reduce pressure, the residue is diluted in the mixture of chloroform/ ethyl ether and then washed with water. The organic layer is dried over anhydrous sodium sulphate and the solvent is evaporated under reduced pressure. 2-(2-Morpholinethyl)-6-amino-2,7-dihydro-3H-dibenzo[de,h]cynnoline-3,7-dione (PDZ-4) is isolated on column chromatography as described in Example 2 in the solvent system, successively, chloroform methanol 50:1; 20:1; 10:1, chloroform-methanol-25% solution of ammonia 5:1:0.1 . The compound is converted into its hydrochloride as described in Example 2. Pale yellow powder is obtained with the yield 60%, melting point 292-295° C.

$^1$H NMR (DMSO-$d_6$) δ=3.10-3.30 (m, 2H); 3.55-4.10 (m, 8H); 4.60 (t, 2H, J=5.7 Hz); 7.40 (d, 1H, J=9.1 Hz); 7.73 (t, 1H, J=6.6 Hz); 7.83 (t, 1H, J=6.4 Hz); 8.20 (d, 1H, J=9.1 Hz); 8.28 (dd, 1H, J=8.1 Hz, J=1.2 Hz); 8.45 (d, 2H, J=7.7 Hz, D$_2$O partly exchangeable); 9.60-9.70 (m, 1H, D$_2$O exchangeable); 10.60-10.70 (m, 1H, D$_2$O exchangeable). MS-FAB m/z (relative intensity, %): 377([M+1)$^+$, 100).

Example 15

2-[3-(Dimethylamino)propyl]-6-amino-2,7-dihydro-3H-dibenzo[de,h]cynnoline-3, 7-dione (PDZ-3), hydrochloride 500 mg (1.7 mmol) of 4-chloroanthraquinone-1-carboxylic acid and 500 mg of phosphorus pentachloride in 5 ml of anhydrous benzene is stirred at room temperature for 50 minutes. The reaction mixture is twice evaporated with anhydrous benzene under reduced pressure, next the precipitate is dissolved in 30 ml anhydrous benzene and during stirring 0.7 ml (5.5 mmol) of 2'-(N,N-dimethylaminopropyl) hydrazine in 12 ml of anhydrous benzene is added dropwise. The progress of the reaction is monitored as described in Example 2. After 20 minutes the reaction mixture is diluted with chloroform, next washed with 5% solution of Na$_2$CO$_3$ and water. The organic layer is dried over anhydrous sodium sulphate and the solvent is evaporated under reduced pressure.

2-[3-(Dimethylamino)propyloamino]-6-chloro-2,7-dihydro-3H-dibenzo [de,h]-3,7-cynnolino-3,7-dione is isolated on column chromatography as described in Example 2 in the solvent system, successively: chloroform-methanol 50:1; 20:1; 10:1. The yield of the isolated product is 55%.

Solution of 48 mg (0.1 mmol) of above obtained compound in 0.8 ml of DMA and 8 ml methanol saturated with gas ammonia in a closed flask is stirred at 65° C. for 3 hours. The progress of the reaction is monitored as described in Example 3. The reaction mixture is evaporated under reduce pressure, the residue is diluted in the mixture of chloroform/ ethyl ether and then washed with water. The organic layer is dried over anhydrous sodium sulphate and the solvent is evaporated under reduced pressure. 2-[3-(Dimethylamino)propyl]-6-amino-2,7-dihydro-3H-dibenzo[de,h]cynnoline-3,7-dione (PDZ-3), is isolated on column chromatography as described in Example 2 in the solvent system, successively: chloroform-methanol 20:1; 10:1; 5:1; chloroform-methanol-25% solution of ammonia 5:1:0.1.

$^1$H NMR (CDCl$_3$) δ=2.1-2.27 (m, 2H); 2.27 (s, 6H); 2.45 (t, 2H, J=6.9 Hz); 4.35 (t, 2H, J=7.3 Hz,); 7.65 (t, 1H, J=6.9 Hz); 7.70 (t, 1H, J=6.8 Hz); 7.95 (d, 1H, J=8.7 Hz); 8.42 (d, 1H, J=6.6 Hz); 8.55 (d, 1H, J=7.6 Hz); 8.65 (d, J=8.6 Hz, 1H); 9.44 (t, 2H, J=4.9 Hz). MS-FAB m/z (relative intensity, %): 349 ([M+1]$^+$, 100).

The compound is converted into its hydrochloride as described in Example 2. Pale yellow powder is obtained with the yield 60%, melting point 309-311° C. (with decomposition).

Example 16

2-[2-(Piperidinamino)ethyl]-6-amino-2,7-dihydro-3H-dibenzo[de,h]-cynnoline-3,7-dione(PDZ-5), hydrochloride 100 mg (0.35 mmol) of 4-chloroanthraquinone-1-carboxylic acid and 100 mg of phosphorus pentachloride in 1.5 ml anhydrous benzene is stirred at room temperature for 40 minutes. The reaction mixture is twice evaporated with anhydrous benzene under reduced pressure, next the precipitate is dissolved in 4.5 ml anhydrous benzene and during stirring at 0° C. 0.3 ml (3 mmol) of 2-(piperidinethyl) hydrazine in 7 ml of anhydrous benzene is added dropwise. The progress of the reaction is monitored as described in Example 2. After 10 minutes the reaction mixture is diluted with chloroform, next washed with 5% solution of Na$_2$CO$_3$ and water. The organic layer is dried over anhydrous sodium sulphate and the solvent is evaporated under reduced pressure. 2-(2-Piperidinethyl)-6-chloro-2,7-dihydro-3H-dibenzo[de,h]cynnoline-3,7-dione is isolated on column chromatography as described in Example 2 in the solvent system, successively: chloroform-methanol 70:1; 50:1; 20:1. The yield of the isolated product is 20%.

Solution of 48 mg (0.1 mmol) above obtained compound in 0.8 ml of DMA and 8 ml methanol saturated with gas ammonia in a closed flask is stirred at 65° C. for 3 hours. The progress of the reaction is monitored as described in Example 3. The reaction mixture is evaporated under reduce pressure, the residue is diluted with the mixture of chloroform ethyl ether and then washed with water. The organic layer is dried over anhydrous sodium sulphate and the solvent is evaporated under reduced pressure. 2-(2-Piperidinethyl)-6-amino-2,7-dihydro-3H-dibenzo[de,h] cynnoline-3,7-dione (PDZ-5) is isolated on column chromatography as described in Example 2 in the solvent system, successively: chloroform-methanol 20:1; 10:1; 5:1; chloroform-methanol-25% solution of ammonia 5:1:0.1.

$^1$H NMR (CDCl$_3$) δ=1.36-1.54 (m, 2H); 1.56-1.75 (m, 4H); 2.55-2.75 (m, 4H); 2.98 (t, 2H, J=7.0 Hz); 4.60 (t, 2H, J=6.9 Hz); 7,01 (d, 1H, J=9.0 Hz); 7.60 (t, 2H, J=7.6 Hz); 7.73 (t, 2H, J=7.3 Hz); 8.27-8.34 (m, 1H); 8.52 (d, 2H, J=7.2 Hz). MS-FAB m/z (relative intensity, %): 375 ([M+1]$^+$, 100).

The compound is converted into its hydrochloride as described in Example 2. Yellow powder is obtained with the yield 60%, melting point 313-315° C. (with decomposition).

Example 17

2-(2-Hydroxyethyl)-6-(2-dimethylamino)ethylamino-2H-dibenzo[de,h]cynnoline-3,7-dione (C-167), hydrochloride 600 mg (2.1 mmol) of 4-chloroanthraquinone-1-carboxylic acid and 600 mg of phosphorus pentachloride in 6 ml anhydrous benzene is stirred at room temperature for 40 minutes. The reaction mixture is twice evaporated with anhydrous benzene under reduced pressure, next the precipitate is dissolved in 30 ml anhydrous benzene and during intensively stirring 0.6 ml of 2-(hydroxyethyl) hydrazine in 10 ml of the mixture tetrahydrofuran/ethanol (the ratio 4/1 by volume) is added dropwise by 15 minutes. The progress of the reaction is monitored as described in Example 2. After 30 minutes the solvent is evaporated under reduced pressure, the residue is dissolved in hot chloroform, then a small amount of silica gel is added and the solvent is again evaporated under reduced pressure.

2-(2-Hydroxyetylo)-6-chloro-2,7-dihydro-3H-dibenzo[de,h]cynnoline-3,7-dion is isolated on column chromatography as described in Example 2 in the solvent system, successively: chloroform-methanol 50:1; 20:1. The yield of the product is 70%.

The solution of 326 mg (1 mmol) of above obtained compound and 0.2 ml (0.15 mmol) of 2-(N,N-dimethylamino) ethylhydrazine in 1 ml of pyridine is stirred at 40° C. for 20 minutes under a nitrogen atmosphere. Progress of the reaction and subsequent procedure are analogous to that described in Example 2.

2-(2-Hydroxyethyl)-6-(2-dimethylamino)ethylamino-2H-dibenzo[de,h]cynnoline-3,7-dione (C-167) is isolated on column chromatography as described in Example 2 in the solvent system, successively: chloroform-methanol 20:1; 10:1; 5:1; chloroform-methanol-25% solution of ammonia 5:1:0.1.

$^1$H NMR (CDCl$_3$) δ=2.40 (s, 6H); 2.75 (t, 2H, J=6.3 Hz); 3.50 (q, 3H, J=6.2 Hz); 4.20 (t, 2H, J=4.8 Hz); 4.60 (t, 2H, J=4.6 Hz); 7.15 (d, 1H, J=9.2 Hz); 7.56-7.70 (m, 2H); 8.30-8.50 (m, 3H); 10.90 (m, 1H, D$_2$O exchangeable). MS-FAB: m/z (relative intensity, %): 379([M+1]$^+$, 100).

The compound is converted into its hydrochloride as described in Example 2. Yellow powder is obtained with the yield 80%, melting point 252-254° C. (with decomposition).

Example 18

2-[2-(Piperidinamino)ethyl]-6-(2-benzylaminoethylamino)-2,7-dihydro-3H-dibenzo [de,h]cynnoline-3,7-dione (PDZ-17), dihydrochloride 36 mg (0.09 mmol) of 2-(2-piperidinoethyl)-6-chloro-2,7-dihydro-3H-dibenzo[de,h]cynnoline-3,7-dione and 0.16 ml of N-benzylethylenediamine in 0.2 ml of pyridine are stirred at 110° C. for 1 hour under nitrogen atmosphere. Progress of the reaction and subsequent procedure are analogous to that described in Example 2. 2-[2-(Piperidinamino) ethyl]-6-(2-benzylaminoethylamino)-2,7-dihydro-3H-dibenzo[de,h] cynnoline-3,7-dione (PDZ-17) is isolated on column chromatography as described in Example 2 in the solvent system, successively: chloroform-methanol 50:1; 20:1; 10:1; 5:1.

$^1$H NMR (CDCl$_3$) δ=1.39-1.55 (m, 2H); 1.56-1.75 (m, 4H), 2.57-2.70 (m, 4H), 2.92-3.09 (m, 4H), 3.50 (q, 2H, J=5.9 Hz); 3.92 (s, 2H); 4.59 (t, 2H, J=7.33 Hz), 7.16-7.43 (m, 7H), 7.58-7.76 (m, 2H), 8.36-8.54 (m, 2H), 11.04 (t, 1H, J=4.9 Hz). MS-FAB m/z (relative intensity, %): 508 ([M+1]$^+$, 100).

The compound is converted into its dihydrochloride as described in Example 2. Dark yellow powder is obtained with the yield 65%, melting point 255-257° C.

Example 19

6-(2-Diethylaminoethyloamino)-2,7-dihydro-3H-dibenzo[de,h]cynnoline-3,7-dione (PDZ-18), hydrochloride 200 mg (0.7 mmol) of 4-chloroanthraquinone-1-carboxylic acid and 200 mg of phosphorus pentachloride in 2 ml of anhydrous benzene is stirred at room temperature to obtain clear solution. Next, to the mixture of 8 ml anhydrous benzene is added. The flask with the reaction mixture is inserted into an ice bath and 0.4 ml of 80% hydrazine is slowly added dropwise. Benzene is evaporated under reduced pressure, then to the residue ammonia is added. Precipitate is filtered, washed with water and dried. 6-Chloro-2,7-dihydro-3H-dibenzo[de,h]cynnoline-3,7-dione is obtained as brown powder with the yield 78%, melting point 316-317° C.

100 mg (0.35 mmol) of above obtained compound and 0.5 ml of N,N-diethylethylenediamine in 0.6 ml of pyridine is stirred at 100° C. for 5 hours under nitrogen atmosphere The progress of the reaction is monitored as described in Example 2. The reaction mixture is diluted with the mixture of chloroform/ethyl ether and to remove excess of amine is washed with diluted solution of hydrochloric acid and next with water. The organic layer is dried over anhydrous sodium sulphate, the solvent is evaporated under reduced pressure. 6-(2-Diethylaminoethyloamino)-2,7-dihydro-3H-dibenzo[de,h]cynnoline-3,7-dione (PDZ-18) is isolated on column chromatography as described in Example 2 in the solvent system, successively: chloroform-methanol 50:1; 20:1; 10:1; 5:1.

$^1$H NMR (CDCl$_3$) δ 1.14 (t, 6H, J=7.2 Hz); 2.65-2.76 (q, 4H, J=7.1 Hz); 2.88 (t, 2H, J=6.6 Hz); 3.51-3.60 (q, 2H, J=6.1 Hz); 7.19-7.26 (d, 1H, J=9.2 Hz); 7.57 (t, 1H, J=7.1 Hz); 7.68 (t, 1H, J=7.2 Hz); 8.32-8.47 (m, 3H), 10.9 (t, 1H, D$_2$O exchangeable), 11.30 (broad singlet, 1H). MS-FAB m/z (relative intensity, %): 363 ([M+1]$^{30}$, 100)

The compound is converted into its hydrochloride as described in Example 2. Dark yellow powder is obtained with the yield 35%, melting point 215-217° C.

Example 20

6-(2-Benzylaminoetyloamino)-2,7-dihydro-3H-dibenzo[de,h]cynnoline-3,7-dione (PDZ-10), hydrochloride 100 mg (0.35 mmol) of 6-chloro-2,7-dihydro-3H-dibenzo[de,h]cynnoline-3,7-dione and 0.5 ml of N-benzylethylenediamine in 1 ml of pyridine is stirred at 104° C. for 5 hours under nitrogen atmosphere. The progress of the reaction is monitored as described in Example 2. Subsequent procedure is analogous to that described in Example 19. 6-(2-Benzyloaminoetyloamino)-2,7-dihydro-3H-dibenzo[de,h]cynnolino-3,7-dion (PDZ-10) is isolated on column chromatography as described in Example 2 in the solvent system, successively: chloroform-methanol 50:1; 20:1; 10:1; 5:1.

The compound is converted into its hydrochloride as described in Example 2. Yellow powder is obtained with the yield 20%, melting point 202-203° C.

$^1$H NMR (d$_6$-DMSO) δ 3.25 (broad singlet, 2H), 3.96 (d, 2H, J=5.8 Hz), 4.21 (d, 2H, J=4.0 Hz), 7.43 (d, 3H, J=7.0 Hz), 7.57-7.65 (m, 3H), 7.70-7.85 (m, 2H), 8.27 (d, 2H, J=8.7 Hz), 8.39 (d, 1H, J=7.9 Hz); 9.52 (broad singlet, 1H, NH, D$_2$O exchangeable), 10.82 (d, 1H, NH, D$_2$O exchangeable, J=6.1 Hz), 13.28 (s, 1H, NH, D$_2$O exchangeable). MS-FAB m/z (relative intensity, %): 396 ([M]$^+$, 100).

Example 21

6-(2-Butylaminoethylamino)-2,7-dihydro-3H-dibenzo[de,h]cynnoline-3,7-dione (PDZ-9), hydrochloride 100 mg (0.35 mmol) of 6-chloro-2,7-dihydro-3H-dibenzo[de,h]cynnoline-3,7-dione and 0.5 ml of N-butylethylenediamine in 1 ml of pyridine is stirred at 104° C. for 5 hours under nitrogen atmosphere. The progress of the reaction is monitored as described in Example 2. Subsequent procedure is analogous to that described in Example 19.

6-(2-Butyloaminoetyloamino)-2,7-dihydro-3H-dibenzo[de,h]cynnolino-3,7-dion (PDZ-9) is isolated on column chromatography as described in Example 2 in the solvent system, successively: chloroform-methanol 50:1; 20:1; 10:1; 5:1.

$^1$H NMR (CDCl$_3$) δ 0.90 (t, 3H, J=7.1 Hz), 1.29-1.40 (m, 2H), 1.62-1.75 (m, 2H), 2.90-3.04 (m, 2H), 3.22-3.37 (m, 2H), 3.89-3.95 (m, 2H), 7.59 (d, 1H, J=9.24 Hz); 7.68 (t, 1H, J=7.4 Hz); 7.80 (t, 1H, J=7.8 Hz); 8.26 (d, 2H, J=9.1 Hz); 8.36 (d, 2H, J=9.3 Hz); 9.09 (s, 1H, D$_2$O exchangeable), 10.78 (s, 1H, J=13.97 Hz); 13.25 (s, 1H, D$_2$O exchangeable). MS-FAB m/z (relative intensity, %): 363 ([M+1]$^+$, 100)

The compound is converted into its hydrochloride as described in Example 2. Yellow powder is obtained with the yield 68%, melting point 203-205° C.

Example 22

6-[(3-Dimethylamino)propyl]amino-3H-dibenzo[de,h]cynnoline-3,7-dione (C-131), hydrochloride Solution of 130 mg (0.5 mmol) of 6-chloro-2,7-dihydro-3H-dibenzo[de,h]cynnoline-3,7-dione and 0.4 ml of N,N-dimethyl-1,3-diamino propane in 1 ml of pyridine is stirred at 100° C. for 210 minutes under nitrogen atmosphere. The progress of the reaction is monitored as described in Example 2. Subsequent procedure is analogous to that described in Example 19.

6-[(3-Dimethylamino)propyl]amino-3H-dibenzo[de,h]cynnoline-3,7-dione (C-131) is isolated on column chromatography as described in Example 2 in the solvent system: chloroform-methanol 10:1, then 5:1. The compound is converted into its hydrochloride as described in Example 2. Dark yellow powder is obtained with the yield 63%, melting point 312-313° C. (with decomposition).

$^1$H NMR (DMSO-d$_6$) δ=2.00-2.20 (m, 2H); 2.78 (s, 3H); 2.80 (s, 3H); 3.10-3.20 (m, 2H); 3.45-3.55 (m, 2H); 7.50 (d, 1H, J=9.2 Hz); 7.70 (t, 1H, J=7.5 Hz); 7.82 (t, 1H, J=7.24 Hz); 8.30 (d, 2H, J=8.4 Hz); 8.40 (d, 1H, J=7.8 Hz); 10.40 (m, 1H, D$_2$O difficultly exchangeable); 10.80 (t, 1H, J=5.3 Hz, D$_2$O difficultly exchangeable); 13.20 (s, 1H, D$_2$O difficultly exchangeable). MS-FAB m/z (relative intensity, %): 349 ([M+1], 100).

Example 23

2-[2-(Dimethylamino)ethyl]-2,7-dihydro-3H-dibenzo[de,h]cynnoline-3,7-dione (PDZ-15), hydrochloride To the suspension of 125 mg (0.125 mmol) of 9,10-dioxo-9,10-dihydro-1-antracene carboxylic acid and 150 mg of phosphorus pentachloride in 2 ml anhydrous benzene is stirred at room temperature for 1 hour. The reaction mixture is evaporated under reduced pressure. To the residue 5 ml anhydrous benzene is added, next during 10 minutes 0.15 ml (1.1 mmol) of 2-(N,N-dimethylamino)ethylhydrazine in 3 ml benzene is added and stirred at room temperature for 1 hour. Progress of the reaction and subsequent procedure is analogous to that described in Example 2. 2-[2-(Dimethylamino)ethylo]-2,7-dihydro-3H-dibenzo [de,h] cynnoline-3,7-dione (PDZ-15) is isolated on column chromatography as described in Example 2 in the solvent system, successively: chloroform-methanol 20:1, then 5:1.

$^1$H NMR (CDCl$_3$) δ=2.49 (s, 6H); 3.05 (t, 2H, J=6.6 Hz); 4.62 (t, 2H, J=6.6 Hz); 7.64 (m, 1H); 7.78 (m, 1H); 7.98 (t, 1H, J=7.7 Hz); 8.38 (dd, 1H, J$_1$=5.0, J$_2$=1.5 Hz); 8.50 (dd, 1H, J$_1$=5.1 Hz, J$_2$=1.3 Hz); 8.74 (m, 2H). MS-FAB m/z (relative intensity, %): 320 ([M+1]$^+$, 100).

The compound is converted into its hydrochloride as described in Example 2. Yellow powder is obtained with the yield 53%, melting point 269-270° C. (with decomposition).

Example 24

2-[2-(Dimethylamino)ethyl]-5-chloro-2,7-dihydro-3H-dibenzo[de,h]cynnoline-3,7-dione Solution of 5 g of phthalic anhydride and 10 g of AlCl$_3$ in 20 ml of m-chlorotoluene is stirred at room temperature for 4 hours. After 150 minutes, when the reaction mixture is thickened, 20 ml of m-chlorotoluene is added. The temperature is gradually raised to 70-75° C. and stirring is continued for next 6 hours. Next, to the reaction mixture, after cooling, 100 ml water is added, and the excess of m-chlorotoluene in evaporated under reduced pressure. Resulting orange precipitate is twice treated with hot water, the residue is heated with diluted solution of $NaHCO_3$, and the solution is filtrated. The filtrate is cooled, and diluted hydrochloric acid is added to precipitate the mixture of two isomers of desired product: 2-(4-chloro-2-methylbenzoilo)-benzoic acid and 2-(2-chloro-2-methylbenzoilo)-benzoic acid.

$^1$H NMR (DMSO-$d_6$) δ=2.50 (s, 3H, $CH_3$); 2.54 (s, 3H, $CH_3$); 7.06 (d, 2H, J=8.2 Hz); 7.21-7.29 (m, 2H); 7.40-7.48 (m, 4H); 7.61-7.68 (m, 4H); 7.85-7.93 (m, 2H); 13.22 (s, 1H) ppm.

Solution of 5 g (18.2 mmol) of above obtained mixture of isomers and 14 ml of 20% oleum is stirred at 100° C. for 90 minutes. Then the reaction mixture is cooled and poured on ice. The resulting grey solid is filtered, washed with water and next is dissolved in solution of NaOH. The insoluble part is separated and to the filtrate diluted hydrochloric acid is added to precipitate mixture of two isomers: 3-chloro-1-methyl-anthraquinone and 1-chloro-3-methyl-anthraquinone.

0.1 g (0.39 mmol) of that isomers mixture, 0.6 ml of water and 3.69 ml of 98% $H_2SO_4$ are stirred at 20° C. to obtain clear solution. The temperature is gradually raised to 70° C. and stirring is continued for next 2 hours. Then 0.264 g of $MnO_2$ is added and stirring is continued for next 2 hours. Then the reaction mixture is cooled and poured on ice, precipitated solid is separated, washed with water and next dissolved in solution of ammonia. The resulted suspension is filtrated and addition of diluted hydrochloric acid precipitated the mixture of 3-chloro-9,10-dioxo-9,10-dihydro-1-anthracenecarboxylic acid and 1-chloro-9,10-dioxo 9,10-dihydro-3anthracenecarboxylic acid.

500 mg (1.7 mmol) of mixture of 3-chloro-9,10-dioxo-9,10-dihydrol-1-anthracenecarboxylic acid/1-chloro-9,10-dioxo-9,10-dihydro-3-anthracene-carboxylic acid and 500 mg of phosphorus pentachloride in 5 ml anhydrous benzene is stirred at 40° C. for 40 minutes. The reaction mixture is twice evaporated with 5 ml benzene under reduced pressure, next the precipitate is dissolved in 30 ml of anhydrous benzene and during stirring, for 20 minutes, 0.6 ml (4.5 mmol) of 2'(N,N-dimethylamino)ethyl hydrazine in 12 ml of benzene is added dropwise. The reaction is continued for next 15 minutes, next 50 ml of chloroform is added, and the solution is washed with 5% solution of $Na_2CO_3$ and water. The organic layer is dried over anhydrous sodium sulphate and the solvent is evaporated under reduced pressure.

2-[2-(Dimethylamino)ethyl]-5-chloro-2,7-dihydro-3H-dibenzo[de,h]cynnoline-3,7-dione is isolated on column chromatography as described in Example 2 in the solvent system, successively: chloroform-methanol 50:1; 20:1. The yield of the isolated product is 47%, melting point 169-172° C.

$^1$H NMR ($C_6D_6$) δ=2.16 (s, 6H, 2x$CH_3$); 2.73 (t, 2H, J=6.3 Hz); 4.33 (t, 2H, J=6.5 Hz); 7.09 (t, 1H, J=7.8 Hz); 7.23 (t, 1H, J=7.3 Hz); 8.29 (d, 1H, J=8.3 Hz); 8.39-8.40 (m, 2H); 8.48 (s, 1H).

Example 25

2-[2-(Dimethylamino)ethyl]-5-[2-(diethylamino)ethyl]-2,7-dihydro-3H-dibenzo[de,h]cynnoline-3,7-dione (C-169), dihydrochloride 80 mg (0.22 mmol) of 2-[2-(dimethylamino)ethyl]-5-chloro-2,7-dihydro-3H-dibenzo[de,h]cynnoline-3,7-dione, 10 mg of CuCl and 0.5 ml of N,N-diethylethylenediamine in 1 ml of pyridine is stirred at 142° C. for 3 hours under nitrogen atmosphere. The progress of the reaction is monitored as described in Example 3. Subsequent procedure is analogous to that described in Example 2. 2-[2-(Dimethylamino)ethyl]-5-[2-(diethylamino)ethyl]-2,7-dihydro-3H-dibenzo [de,h] cynnoline-3,7-dione (C-169) is isolated on column chromatography as described in Example 2 in the solvent system, successively: chloroform-methanol 50:1; 30:1; 10:1; 5:1, then chloroform-methanol-25% solution of ammonia 5:1:0.1.

$^1$H NMR (CDCl$_3$) δ=1.13 (t, 6H, J=7.0 Hz); 2.42 (s, 6H); 2.75 (q, 4H, $J_1$=6.7 Hz, $J_2$ =2Hz); 2.90 (t, 4H, J=6.31 Hz); 3.39 (q, 2H, $J_1$=5.1 Hz, $J_2$=2.1 Hz); 4.49 (t, 2H, J=7.6 Hz); 5.85 (s, 1H); 7.55 7.70 (m, 3H); 7.88 (d, 1H, J=2.3 Hz); 8.30 (d, 1H, J=7.0 Hz); 8.43 (d, 1H, J=7.7 Hz). MS-FAB m/z (relative intensity, %): 434 ([M+1]$^+$, 100).

The compound is converted into its dihydrochloride as described in Example 2. Yellow powder is obtained with the yield 18%, melting point 108-110° C.

Example 26

2-[2-(Dimethylamino)ethyl]-5-(2-aminoetyloamino)-2,7-dihydro-3H-dibenzo[de,h]cynnoline-3,7-dione (C-170), dihydrochloride 80 mg (0.22 mmol) of 2-[2-(dimethylamino)ethyl]-5-chloro-2,7-dihydro-3H-dibenzo[de,h]cynnoline-3,7-dione, 10 mg of CuCl and 0.5 ml of 1,2diaminoethane in 1 ml of pyridine is stirred at 112° C. for 3 hours under nitrogen atmosphere. The progress of the reaction is monitored as described in Example 3. Subsequent procedure is analogous to that described in Example 2.

2-[2-(Dimethylamino)ethyl]-5-(2aminoetyloamino)-2,7-dihydro-3H-dibenzo [de,h]cynnoline-3,7-dione (C-170) is isolated on column chromatography as described in Example 2 in the solvent system, successively: chloroform-methanol 50:1; 30:1; 10:1; 5:1, then chloroform-methanol-25% solution of ammonia 5:1:0.1.

$^1$H NMR (CDCl$_3$) δ=2.37 (s, 6H); 2.84 (t, 2H, J=6.6 Hz); 3.14 (t, 2H, J=5.8 Hz); 3.40 (m, 2H); 4.40 (t, 2H, J=4.4 Hz); 5.50 (s, 1H); 7.44-7.72 (m, 3H); 7.81(d, 1H, J=2.2 Hz); 8.23 (d, 1H, J=7.7 Hz); 8.37 (d, 1H, J=8.0 Hz) ppm. MS-FAB m/z (relative intensity, %): 378 ([M+1]$^+$, 100).

The compound is converted into its dihydrochloride as described in Example 2. Yellow powder is obtained with the yield 18%, melting point 285-288° C.

Example 27

2-[2-(Dimethylamino)ethyl]-5-[(2-benzylamino)ethylamino]-2,7-dihydro-3H-dibenzo[de,h]cynnolino-3,7-dion (C 171), dihydrochloride 50 mg (0.17 mmol) of 2-[2-(dimethylamino)ethyl]-5-chloro-2,7-dihydro-3H-dibenzo[de,h]cynnoline-3,7-dione, 8 mg of CuCl and 0.5 ml of N-benzyletylenediamine in 1 ml of pyridine is stirred at 156° C. for 4 hours under nitrogen atmosphere. The progress of the reaction is monitored as described in Example 3. Subsequent procedure is analogous to that described in Example 2.

2-[2-(Dimethylamino)ethyl]-5-[(2-benzylamino)etylamino]-2,7-dihydro-3H-dibenzo[de,h]cynnolino-3,7-dione (C-171) is isolated on column chromatography as described in Example 2 in the solvent system, successively: chloroform-methanol 50:1; 30:1; 10:1; 5:1, then chloroform-methanol-25% solution of ammonia 5:1:0.1. Melting point 109-111° C.

$^1$H NMR (CDCl$_3$) δ=2.42 (s, 6H); 2.95 (t, 2H, J=6.3 Hz); 3.10 (s, 2H); 3.48 (d, 2H, J=4.5 Hz); 4.03 (s, 2H); 4.49 (t, 2H, J=6.8 Hz); 7.34 (m, 5H); 7.43 (s, 3H); 7.72 (s, 1H); 8.16 (d, 1H, J=7.8 Hz); 8.26 (d, 1H, J=7.8 Hz). MS-FAB m/z (relative intensity, %): 468 ([M+1]$^+$, 100).

The compound is converted into its dihydrochloride as described in Example 2. Yellow powder is obtained with the yield 15%.

Example 28

Bis-2,6-[2-(dimethylamino)ethyl]-2,6-dihydro-5H-benzo[h]indazolo[5,4,3-def]cynnoline-5-one (C-163), hydrochloride To the suspension of 180 mg (0.5 mmol) of 2-[2-(dimethylamino)ethyl]-6-chloro-2,7-dihydro-3H-dibenzo[de,h]cynnoline-3,7-dione in 2 ml of DMSO and 0.15 ml chloroform is intensively stirred at 90° C., then 0.5 ml (3.75 mmol) of 2-(dimethylethyl)hydrazine is added dropwise. The progress of reaction is monitored as described in Example 2. After 80 minutes subsequent procedure is analogous to that described in Example 2.

Bis-2,6-[2-(dimethylamino)ethyl]-2,6-dihydro-5H-benzo[h]indazolo[5,4,3-def]cynnoline-5-one (C-163) is isolated on column chromatography as described in Example 2 in the solvent system, successively: chloroform-methanol 50:1; 20:1; 5:1;2:1.

$^1$H NMR (CDCl$_3$) δ=2.30 (s, 6H); 2.45 (s, 6H); 3.00 (t, 4H, J=6.0 Hz); 4.70 I 4.75 (two overlapping triplet, 4H); 7.60-7.70 (m, 2H); 7.80 (d, 1H, J=8.8 Hz); 8.30 (d, 1H, J=8.9 Hz); 8.35 (m, 1H); 8.70-8.80 (m, 1H). MS-FAB: m/z (relative intesity, %); 403 ([M+1]$^+$, 100), 357([M−45], 30).

The compound is converted into its dihydrochloride as described in Example 2. Yellow-orange powder is obtained with the yield 40%, melting point 243.5-245° C.

Example 29

2,7-Bis-[2-(diethylamino)ethyl]-2,7-dihydrobenzo[h]pthtalazyno[7,8,1-def]cynnoline-3,6-dion (CP-4), dihydrochloride To the suspension of 200 mg (0.7 mM) of 9,10-dioxo-9,10-dihydro-1,4-anthracene dicarboxylic acid and 400 mg of phosphorus pentachloride in 5 ml anhydrous benzene is refluxed for 1 hour. The reaction mixture is evaporated under reduced pressure, then 0.8 ml of 2-(N,N-diethylamino)ethylhydrazine in 10 ml benzene is added dropwise at 90° C. The progress of reaction is monitored as described in Example 2. The reaction mixture is evaporated under reduced pressure, next diluted with chloroform, then washed with solution of NaHCO$_3$ and water. The organic layer is dried over anhydrous sodium sulphate and the solvent is evaporated under reduced pressure. 2,7-Bis[2-(diethylamino)ethyl]-2,7-dihydrobenzo[h]pthtalazyno[7,8,1-def]cynnoline-3,6-dion (CP-4) is isolated on column chromatography as described in Example 2 in the solvent system, chloroform-methanol-25% solution of ammonia 150:15:1

$^1$H NMR (CCl$_3$) δ=1.10 (t, 12H, J=7.0 Hz); 2.72 (q, 8H, J=7.3 Hz); 3.10 (t, 4H, J=7.3 Hz); 4.60 (t, 4H, J=7.3 Hz); 7.66 (q, 2H, J=3.4 Hz); 8.57 (q, 2H, J=3.4 Hz); 8.60 (s, 2H). MS-FAB: m/z (relative intensity, %); 486 ([M]$^+$, 100)

The compound is converted into its dihydrochloride as described in Example 2. Yellow powder is obtained with the yield 30%, melting point 275-276° C.

The invention claimed is:

1. Asymmetrically substituted anthrapyridazone derivatives of formula (I)

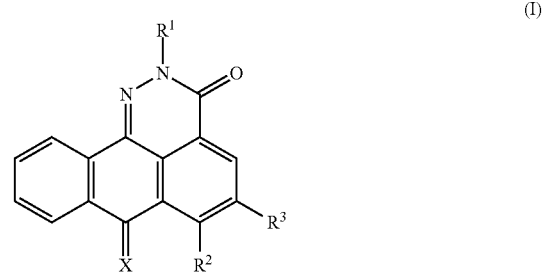

wherein
X is oxygen or nitrogen atom,
and
when X is oxygen atom, then anthrapyridazone is presented by formula (IA)

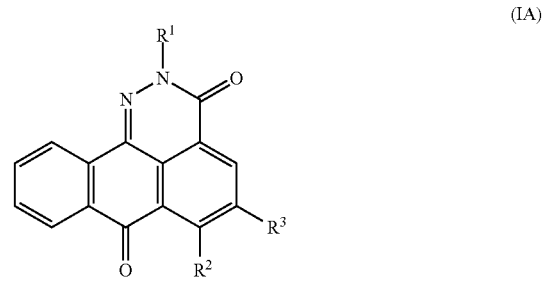

wherein only one of three substituents $R^1$, $R^2$ or $R^3$ is hydrogen atom, while the two remaining substituents, have the following meaning:
$R^1$ is —(CH$_2$)$_q$—OH or —(CH$_2$)$_q$—N(R$^4$)—R$^5$,
where
q=2 or 3;
$R^4$ and $R^5$ are the same and mean C$_1$ or C$_3$-alkyl,
or
$R^4$ and $R^5$ together with the nitrogen atom at position 2 to which they are attached form 6-membered cyclic ring optionally containing additional nitrogen or oxygen atoms;
$R^2$ is —NH—(CH$_2$)$_m$—(Y)$_n$—(CH$_2$)$_p$—R$^6$,
where
m=1, 2 or 3
n=1
p=1 or 2
Y is —C(O)— or —N(R$^7$)—
$R^6$ is —OH or phenyl,
$R^7$ is hydrogen atom or C$_1$-C$_3$-alkyl,
$R^3$ is hydrogen atom or —NH—(CH$_2$)$_r$—N(R$^8$)—R$^9$ moiety
where
r=1, 2 or 3,
$R^8$ and $R^9$ are the same or different and independently are H, C$_1$-C$_3$-alkyl or phenyl substituted with C$_1$-C$_3$-alkyl;
with the provision, that when $R^1$ is —$(CH_2)_2N(CH_3)_2$ (q=2 and $R^4=R^5=CH_3$), then
$R^2$ is not —$(CH_2)_2N(CH_3)_2$ nor —$NH_2$;
and
when X is nitrogen atom, then in formula (I)
$R^3$ is H,
$R^2$ is attached to nitrogen atom and together form the group presented by formula (a) or (b)

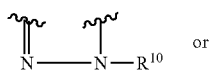
(a)

or

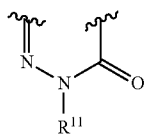
(b)

$R^1$ and $R^{10}$ are the same and are —$(CH_2)_2N(CH_3)_2$, and
$R^1$ and $R^{11}$ are the same and are —$(CH_2)_2N(CH_2CH_3)_2$,
thus anthrapyridazone has the formula (I B) or (I C)

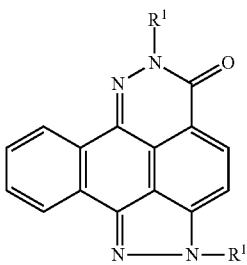
(IB)

or

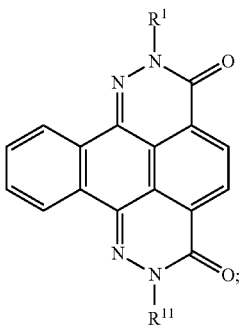
(IC)

as well as their pharmaceutically acceptable salts.

2. Anthrapyridazone derivatives according to claim 1 of formula (IA), wherein
X represents oxygen atom,
$R^1$ is —$(CH_2)_2N(CH_3)_2$,
$R^2$ is —NH—$(CH_2)_m$—$(Y)_n$—$(CH_2)_p$—$R^6$,
where
m=0, 1, 2 or 3
n=0, 1
p=0, 1, 2
Y is —$N(R^7)$—
$R^6$ is hydrogen atom or —OH,
$R^7$ is hydrogen atom or $C_1$-$C_3$-alkyl, and
$R^3$ is hydrogen atom.

3. Asymmetrically substituted anthrapyridazone derivatives of formula (I)

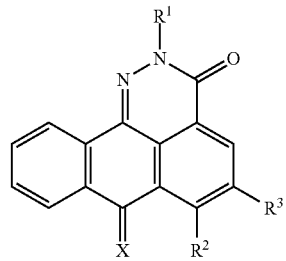
(I)

wherein
X is oxygen or nitrogen atom,
and
when X is oxygen atom, then anthrapyridazone is presented by formula (IA)

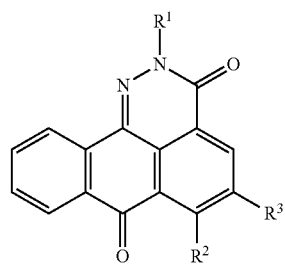
(IA)

wherein only one of three substituents $R^1$, $R^2$ or $R^3$ is hydrogen atom, while the two remaining substituents, have the following meaning:
$R^1$ is —$(CH_2)_q$—$N(R^4)$—$R^5$,
where
q=2 or 3,
$R^4$ and $R^5$ together with a nitrogen atom at position 2 to which they are attached form 6-membered cyclic ring possibly including additional nitrogen or oxygen atom;
$R^2$ is —NH—$(CH_2)_m$—$(Y)_n$—$(CH_2)_p$—$R^6$,
where
m=0, 1, 2 or 3
n=0, 1
p=0, 1, 2
Y is —$N(R^7)$— group
$R^6$ is hydrogen atom or —OH, and
$R^7$ is hydrogen atom or —$CH_3$, and
$R^3$ is H.

4. Anthrapyridazone derivatives according to claim 1 of formula (IA), wherein
$R^1$ is H
$R^2$ is —NH—$(CH_2)_m$—$(Y)_n$—$(CH_2)_p$—$R^6$,
where
m =0, 1, 2 or 3
n=0 or 1
p=0, 1 or 2
Y is —$N(R^7)$—
$R^6$ is hydrogen atom or —OH,
$R^7$ is hydrogen atom or —$CH_3$,
$R^3$ is H.

5. Anthrapyridazone derivatives according to claim 1 of formula (IA), wherein
$R^1$ is —$(CH_2)_2N(CH_3)_2$,
$R^2$ is H, R³ is hydrogen atom or —NH—(CH₂)ᵣ—N(R⁸)—R⁹, where
r=2,
R⁸ and R⁹, are the same or different and mean H, C₁-C₃-alkyl or C₁-C₃-phenyl.

6. Anthrapyridazone derivatives according to claim 1 selected from the group comprising:

2-[2-(Dimethylamino)ethyl]-6-{[2-(methylamino)ethyl]amino}-2,7-dihydro-3H-dibenzo[de,h]cynnoline-3,7-dione,
2-[2-(Dimethylamino)ethyl]-6-[2-(aminoethyl)amino)-2,7-dihydro-3H-dibenzo [de,h]cynnoline-3,7-dione,
2-[2-(Dimethylamino)ethyl]-6-(N-methylamino)-2,7-dihydro-3H-dibenzo[de,h]cynnoline-3,7-dione,
2-[2-(Dimethylamino)ethyl]-6-{[2-(ethylamino)ethyl]amino}-2,7-dihydro-3H-dibenzo[de,h]cynnoline-3,7-dione,
2-[2-(Dimethylamino)ethyl]-6-[(3-aminopropyl)amino]-2,7-dihydro-3H-dibenzo[de,h]cynnoline-3,7-dione,
2-[2-(Dimetyloamino)etyl]-6-[(3-acetyloaminopropyl)amino]-2,7-dihydro-3H-dibenzo[de,h]cynnolino-3,7-dione,
2-[2-(dimethylamino)ethyl]-6-(acetylamino)-2,7-dihydro-3H-dibenzo[de,h]cynnoline-3,7-dione,
2-[2-(Dimethylamino)ethyl]-6-{[(2-diethylamino)ethyl]amino}-2,7-dihydro-3H-dibenzo[de,h]cynnoline-3,7-dione,
2-[2-(Dimethylamino)ethyl]-6-(N-benzylamino)-2,7-dihydro-3H-dibenzo[de,h]cynnoline-3,7-dione,
2-[2-(Dimethylamino)ethyl]-6-[2-(2-aminoethylamino)etanolo]-2,7-dihydro-3H-dibenzo[de,h]cynnoline-3,7-dione,
2-[2-(Dimethylamino)ethyl]-6-[(N,N-dimethyloacetamido)amino]-2,7-dihydro-3H-dibenzo[de,h]cynnolin-3,7-dione,
2-[2-(Dimethylamino)propyl]-6-{[2-(dimethylamino)propyl]amino}-2,7-dihydro-3H-dibenzo[de,h]cynnoline-3,7-dione,
2-(2-Morpholinethyl)-6-amino-2,7-dihydro-3H-dibenzo[de,h]cynnoline-3,7-dione,
2-[3-(Dimethylamino)propyl]-6-amino-2,7-dihydro-3H-dibenzo[de,h]cynnoline-3,7-dione,
2-[2-(Piperidinamino)ethylo]-6-amino-2,7-dihydro-3H-dibenzo[de,h]cynnoline-3,7-dione,
2-(2-Hydroxyethyl)-6-(2-dimethylamino)ethylamino-2H-dibenzo[de,h]cynnoline-3,7-dione,
2-[2-(Piperidinamino)ethyl]-6-(2-benzylaminoethylamino)-2,7-dihydro-3H-dibenzo[de,h]cynnoline-3,7-dione,
6-(2-Diethylaminoethylamino)-2,7-dihydro-3H-dibenzo[de,h]cynnoline-3,7-dione,
6-(2-Benzylaminoethylamino)-2,7-dihydro-3H-dibenzo[de,h]cynnoline-3,7-dione,
6-(2-Butylaminoethylamino)-2,7-dihydro-3H-dibenzo[de,h]cynnoline-3,7-dione,
6-[(3-Dimethylamino)propyl]amino-3H-dibenzo[de,h]cynnolin-3,7-dione,
2-[2-(Dimethylamino)ethyl]-2,7-dihydro-3H-dibenzo[de,h]cynnoline-3,7-dione,
2-[2-(Dimethylamino)ethyl]-5-[2-(diethylamino)ethyl]-2,7-dihydro-3H-dibenzo[de,h]cynnoline-3,7-dione,
2-[2-(Dimethylamino)ethyl]-5-(2-aminoethylamino)-2,7-dihydro-3H-dibenzo[de,h]cynnoline-3,7-dione,
[2-(Dimethylamino)ethyl]-5-[(2-benzylamino)ethylamino]-2,7-dihydro-3H-dibenzo[de,h]cynnoline-3,7-dione
Bis-2,6-[2-(dimethylamino)ethyl]-2,6-dihydro-5H-benzo[h]indazolo[5,4,3-def]cynnoline-5-one,
2,7-Bis-[2-(diethylamino)ethyl]-2,7-dihydrobenzo[h]ftalazyno[7,8,1-def]cynnoline-3,6-dione,
as well as their pharmaceutically acceptable salts.

7. An anthrapyridazone, which is 2-[2-(dimethylamino)ethyl]-6-(2-aminoethylamino)-2,7-dihydro-3H-dibenzo[de,h]cynnoline-3,7-dione, represented by formula:

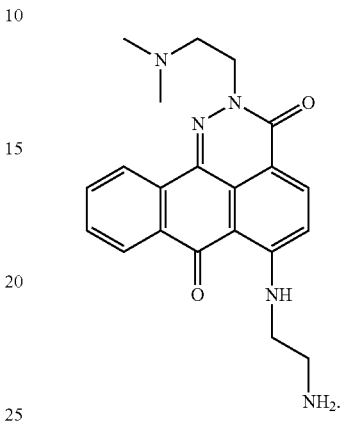

8. An anthrapyridazone, which is 2-[2-(dimehtylamino)ethyl]-6-(2-aminoethylamino)-2,7-dihydro-3H-dibenzo[de,h]cynnoline-3,7-dione represented by formula:

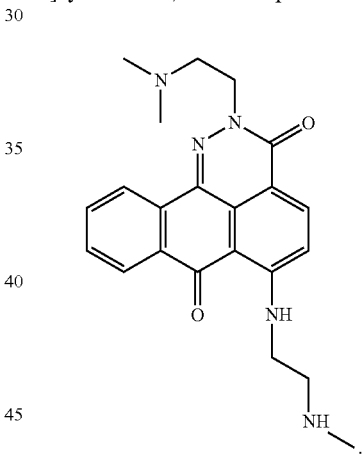

9. An anthrapyridazone, which is bis-2,6-[2-(dimethylamino)ethyl]-2,6-dihydro-5H-benzo[h]indazolo[5,4,3-def]cynnoline-5-one, represented by formula:

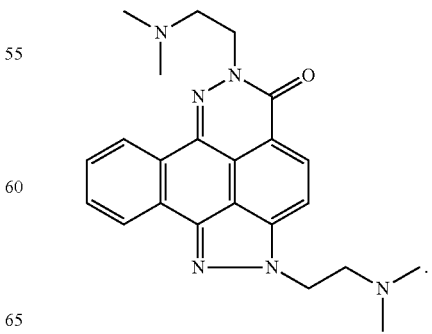

10. An anthrapyridazone, which is 2,7-bis-[2-(diethyl-lamino)ethyl]-2,7-dihydrobenzo[h]ftalazyno[7,8,1-def]cyn-noline-3,6-dione, represented by formula:

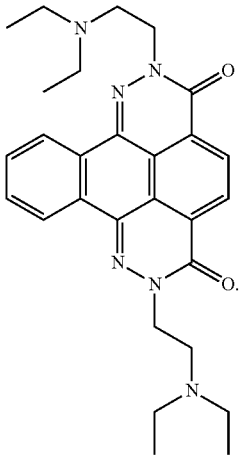 [SMILES: CCN(CC)CCn1nc2c3ccccc3c3nn(CCN(CC)CC)c(=O)c4ccc(c1=O)c2c43]

11. Anthrapyridazone derivatives of formula (I) defined in claim 1 configured to be used as the medicines exhibiting the activity against tumor cells.

12. Anthrapyridazone derivatives of formula (I) defined in claim 1 configured to be used as the medicines in the treatment of neoplastic diseases in oncologic patients.

13. Anthrapyridazone derivatives of formula (I) defined in claim 1 configured to be used, together with the other chemotherapeutic, in the treatment of patients with diagnosed resistance resulting from overexpression simultaneously of several types of exporting proteins.

14. Pharmaceutical formulation comprising as active substance anthrapyridazone of formula (I) defined in claim 1 in therapeutically effective amount together with pharmaceutically acceptable carriers and/or auxiliary substances.

15. A method of treatment of patients, comprising administering to a patient a therapeutically effective amount of anthrapiridazone of formula (I),

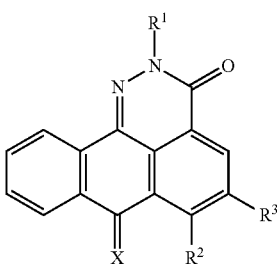

wherein
X is oxygen or nitrogen atom,
and
when X is oxygen atom, then anthrapyridazone is presented by formula (IA)

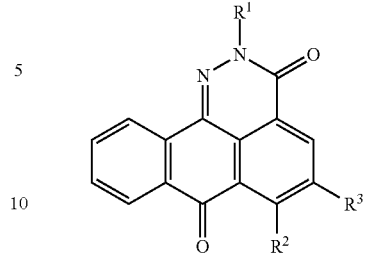

wherein only one of three substituents R1, R2 or R3 is hydrogen atom, while the two remaining substituents, have the following meaning:

R1 is (CH2)q-OH or —(CH2)q-N(R4)—R5,
where
q=2 or 3;
R4 and R5 are the same and mean C1 or C3-alkyl,
or
R4 and R5 together with the nitrogen atom at position 2 to which they are attached form 6-membered cyclic ring optionally containing additional nitrogen or oxygen atoms, such as piperazine, piperidine or morpholine rings;
R2 is —NH—(CH2)m-(Y)n-(CH2)p-R6,
where
m=1, 2 or 3
n=1
p=1 or 2
Y is —C(O)— or —N(R7)—
R6 is —OH or phenyl,
R7 is hydrogen atom or C1-C3-alkyl,
R3 is hydrogen atom or —NH—(CH2)r-N(R8)-R9 moiety
where
r=1, 2 or 3,
R8 and R9 are the same or different and independently are H, C1-C3-alkyl or phenyl substituted with C1-C3-alkyl;
with the provision, that
when R1 is —(CH2)2N(CH3)2 (q=2 and R4=R5=CH3), then R2 is not —(CH2)2N(CH3)2 nor —NH2;
and
when X is nitrogen atom, then in formula (I)
R3 is H,
R2 is attached to nitrogen atom and together form the group presented by formula (a) or (b)

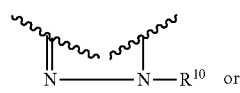

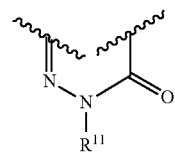

R1 and R10 are the same and are —(CH2)2N(CH3)2, and
R1 and R11 are the same and are —(CH2)2N(CH2CH3)2,
thus anthrapyridazone has the formula (I B) or (I C)
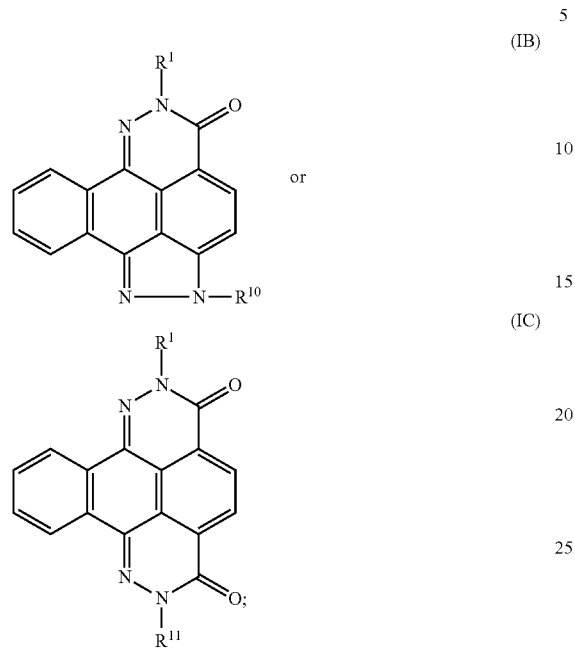
as well as their pharmaceutically acceptable salts.
* * * * *